US008314246B2

(12) United States Patent
Jamison et al.

(10) Patent No.: US 8,314,246 B2
(45) Date of Patent: Nov. 20, 2012

(54) CATALYTIC REACTIONS INVOLVING ALKENES

(75) Inventors: Timothy F. Jamison, Cambridge, MA (US); Sze-Sze Ng, Midland, MI (US)

(73) Assignee: Massachusetts Institute of Technology, Cambridge, MA (US)

(*) Notice: Subject to any disclaimer, the term of this patent is extended or adjusted under 35 U.S.C. 154(b) by 801 days.

(21) Appl. No.: 11/991,340

(22) PCT Filed: Aug. 30, 2006

(86) PCT No.: PCT/US2006/033829
§ 371 (c)(1),
(2), (4) Date: Apr. 17, 2009

(87) PCT Pub. No.: WO2007/027752
PCT Pub. Date: Mar. 8, 2007

(65) Prior Publication Data
US 2009/0216025 A1   Aug. 27, 2009

Related U.S. Application Data

(60) Provisional application No. 60/712,360, filed on Aug. 30, 2005.

(51) Int. Cl.
*C07D 231/00* (2006.01)
(52) U.S. Cl. .................................................. 548/110
(58) Field of Classification Search .................. 548/110
See application file for complete search history.

(56) References Cited

U.S. PATENT DOCUMENTS 3,960,973 A    6/1976  Stapp
4,126,751 A *  11/1978 Stapp ............................ 568/879

OTHER PUBLICATIONS

Wender et al. CAS: 149:307099, 2001.*
Adams et al., "The Prins Reaction," *Synthesis* 1977, 661-672.
Arundale, E. et. al., "The Olefin-Aldehyde Condensation: The Prins Reaction," *Chem. Rev.* 1952, 52, 505-555.
Brandsma et al., "The first successful direct metallation of ethene," J. Chem. Soc., Chem. Comm. 1986, 260.
Crowe et al., "Titanium-Catalyzed Reductive Cyclization of δ,ε-Unsaturated Ketones and Aldehydes," *J. Am. Chem. Soc.* 1995, 117, 6787.
Hayashi, M., "Fluoride-catalyzed three-component coupling reaction of a silylphosphine, activated alkenes and aldehydes," *Tet Lett.* 2005, 46, 5135-5138.
Huang et al., "Highly Selective Catalytic Intermolecular Reductive Coupling of Alkynes and Aldehydes," *Org. Lett.* 2000, 2, 4221-4223.
Jang et al., "Hydrogen-Mediated C—C Bond Formation: Catalytic Regio- and Stereoselective Reductive Condensation of α-Keto Aldehydes and 1,3-Enynes," *J. Am. Chem. Soc.* 2004, 126, 4664-4668.
Jang et al., *Angew. Chem. Int. Ed.* 2003, 42, 4074-4077.

Jang et al., "Reductive Generation of Enolates from Enones Using Elemental Hydrogen: Catalytic C—C Bond Formation under Hydrogenative Conditions," *J. Am. Chem. Soc.* 2002, 124, 15156-15157.
Kablaoui et al., "Reductive Cyclization of Enones by a Titanium Catalyst," *J. Am. Chem. Soc.* 1995, 117, 6785-6786.
Kimura et al., "Novel and Highly Regio- and Stereoselective Nickel-Catalyzed Homoallylation of Benzaldehyde with 1,3-Dienes," *J. Am. Chem. Soc.* 1998, 120, 4033-4034.
Marriner et al., "Metallo-Aldehyde Enolates via Enal Hydrogenation: Catalytic Cross Aldolization with Glyoxal Partners As Applied to the Synthesis of 3,5-Disubstituted Pyridazines," *J. Org. Chem.* 2003, 69, 1380-1382.
Matsuda et al., *Tetrahedron Lett.* 1990, 31, 5331-5334.
Miller et al., "Catalytic Asymmetric Reductive Coupling of Alkynes and Aldehydes: Enantioselective Synthesis of Allylic Alcohols and α-Hydroxy Ketones," *J. Am. Chem. Soc.* 2003, 125, 3442-3443.
Montgomery, J., *Angew. Chem. Int. Ed.* 2004, 43, 3890-3908.
Ng et al.., "Simple Alkenes as Substitutes for Organometallic Reagents: Nickel-Catalyzed, Intermolecular Coupling of Aldehydes, Silyl Triflates, and Alpha Olefins," *J. Am. Chem. Soc.* 2005, 127(41), 14194.
Ng et al., "Highly Enantioselective and Regioselective Nickel-Catalyzed Coupling of Allenes, Aldehydes, and Silanes," *J. Am. Chem. Soc.* 2005, 127, 7320-7321.
Ng et al., "Nickel-Catalyzed Coupling of Alkenes, Aldehydes, and Silyl Triflates," *J. Am. Chem. Soc.* 2006, 128, 11513-11528, as publised online Aug. 10, 2006.
Ogoshi et al., "Direct Observation of Oxidative Cyclization of η²-Alkene and η²-Aldehyde on Ni(0) Center. Significant Alteration by Addition of Me₃-SiOTf," *J. Am. Chem. Soc.* 2004, 126(38), 11802.
Og
oshi et al., "AlMe₃-Promoted Oxidative Cyclization of η²-Alkene and η²-Ketone on Nickel(0). Observation of Intermediate in Methyl Transfer Process," *J. Am. Chem. Soc.* 2005, 127(37), 12810-12811.
Oblinger et al., "A New Stereoselective Method for the Preparation of Allylic Alcohols," *J. Am. Chem. Soc.* 1997, 119, 9065-9066.
Oblinger, E. S., "Nickel-Catalyzed and Organozinc-Mediated Carbocyclizations and Three-Component Couplings," (Ph.D. Thesis, Wayne State University, 1997), 88 pages.
Ramón et al., *Angew. Chem. Int. Ed.* 2005, 44, 1602-1634.
Revis et al., *Tetrahedron Lett.* 1987, 28, 4809-4812.

(Continued)

*Primary Examiner* — Rei-tsang Shiao
(74) *Attorney, Agent, or Firm* — Wolf, Greenfield & Sacks, P.C.

(57) ABSTRACT

The present invention relates to new compositions and reactions to produce allylic alcohols or precursors of allylic alcohols (e.g., silyl ethers of allylic alcohols). Methods of the invention may comprise combining an alkene and an aldehyde in the presence of a transition metal catalyst (e.g., a nickel catalyst) to form an allylic alcohol or precursor of an allylic alcohol. Reaction products of the present invention may be valuable as intermediates and/or products in pharmaceutical and polymer research. Also, methods of the invention may be useful as fragment coupling reactions in complex molecule synthesis. Moreover, methods of the invention may include the use of reagents which, under reaction conditions known in the art, may have been unreactive, i.e., may not have been able to form the reaction product. The reagents used in the present invention may be relatively lower in cost than in other methods. Also, methods of the invention may reduce the number of synthetic and purification steps required to produce the reaction products, as well as reducing time, cost, and waste production.

14 Claims, 13 Drawing Sheets

OTHER PUBLICATIONS

Sato et al., "Nickel-Catalyzed Intermolecular Coupling of 1,3-Dienes and Aldehydes via Transmetalation of Nickelacycles with Diisobutylaluminum Acetylacetonate," *J. Org. Chem.* 2002, 67, 656-662.

Takai et al., "Regioselective Reductive Coupling of Alkynes and Aldehydes Leading to Allylic Alcohols," *Org. Lett.* 2003, 5, 653-656.

Taylor et al., "Catalytic Diastereoselective Reductive Aldol Reaction: Optimization of Interdependent Reaction Variables by Arrayed Catalyst Evaluation," *J. Am. Chem. Soc.* 1999, 121, 12202-12203.

Trost et al., "Non-metathesis ruthenium-catalyzed C—C bond formation," *Chem. Rev.* 2001, 101, 2067-2096.

Tsujimoto, S., "Addition of aldehydes and their equivalents to electron-deficient alkenes using N-hydroxyphthalimide (NHPI) as a polarity-reversal catalyst," *Tet Lett.* 2003, 44, 5601-5604.

International Search Report and Written Opinion, mailed Jan. 2, 2007, in PCT/US2006/033829, 2007.

International Preliminary Report on Patentability, mailed Mar. 4, 2008, in PCT/US2006/033829, 2008.

Wender et al., "Bis(1.5-cyclooctadiene)nickel(0)," *Encyclopedia of Reagents for Organic Synthesis*, Article Online Posting Date: Sep. 15, 2006, 44 pages.

* cited by examiner

FIGURE 1B $$H_2C=CH_2 \quad + \quad \underset{R}{\overset{O}{\underset{H}{\bigvee}}} \quad \xrightarrow[\text{Toluene, rt}]{\text{Ni(cod)}_2, \text{Ligand}, R_3\text{SiOTf}, Et_3N} \quad \underset{R}{\overset{OSiEt_3}{\bigvee}}$$
1

| entry | R (aldehyde) | R₃SiOTf | product | isolated yield (%) | entry | R (aldehyde) | R₃SiOTf | product | isolated yield (%) |
|---|---|---|---|---|---|---|---|---|---|
| 1 | Ph | Et₃SiOTf | 1a | 82 (65)[b] | 8 | 2-Me-indol-3-yl | Et₃SiOTf | 1h | 80 |
| 2 | p-tolyl | Et₃SiOTf | 1b | 88 (65)[b] | 9 | 2-furyl | Et₃SiOTf | 1i | 38 |
| 3 | o-tolyl | Et₃SiOTf | 1c | 93 (64)[b] | 10 | p-CF₃-C₆H₄ | Et₃SiOTf | 1j | 25 |
| 4 | p-anisyl | Et₃SiOTf | 1d | 95 (65)[c] | 11[f] | p-CO₂Me-C₆H₄ | Et₃SiOTf | 1k | 34 |
| 5 | 2-naphthyl | Et₃SiOTf | 1e | 95 (83)[c] | 12 | piv | Et₃SiOTf | 1l | 70 |
| 6 | 2-naphthyl | Me₃SiOTf | 1f | 60 | 13 | CMe₂CO₂Me | Et₃SiOTf | 1m | 81 (40)[c,d] |
| 7 | 2-naphthyl | t-BuMe₂SiOTf | 1g | 67 | 14 | cyclohexyl | Et₃SiOTf | 1n | 25[e] (34)[d,e] |

[a] Standard procedure: Ni(cod)₂ (20 mol %) and (o-anisyl)₃P (40 mol %) were dissolved in 2.5 mL of toluene under argon. Ethylene (balloon, 1 atm) was substituted for argon. Triethylamine (600 mol %), the aldehyde (100 mol %, 0.5 mmol), and Et₃SiOTf (175 mol %) were added. The reaction mixture was stirred for 6–18 h at 23 °C. [b] (o-anisyl)₃P was replaced by Cy₂PhP. [c] (o-anisyl)₃P was replaced by Ph₃P. [d] Yields determined by ¹H NMR using DMF as a standard. [e] Conducted under 2 atm of ethylene. [f] Stirred at room temperature for 30 h.

FIGURE 4

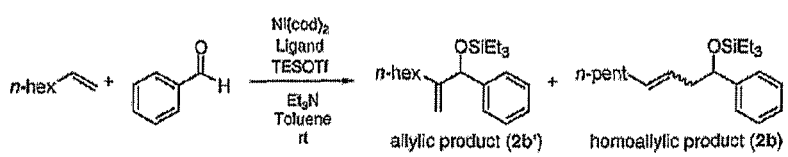

| entry | ligand | cone angle | ν$_{CO}$ | yield (2b') [c] | yield (2b) [c] | ratio (2b':2b) [d] | combined yield (2b'+2b) |
|---|---|---|---|---|---|---|---|
| 1 | (n-Bu)$_3$P | 132 | 1915 | 11% | 27% | 29:71 | 38% |
| 2 | (n-Oct)$_3$P | 107 | | 7% | 14% | 23:77 | 21% |
| 3 | (i-Pr)$_3$P | 160 | 1915 | 11% | 2% | 85:15 | 13% |
| 4 | Cyp$_3$P | | | 10% | 3% | 78:22 | 13% |
| 5 | Cy$_3$P | 170 | 1915 | 13% | 3% | 81:19 | 16% |
| 6 | (t-Bu)$_3$P | 182 | | 7% | 2% | 78:22 | 9% |
| 7 | Cy$_2$PhP | 162 | 1917 | 37% | 16% | 70:30 | 53% |
| 8 [e] | Cy$_2$(o-tol)P | 161 | | 30% | 5% | 86:14 | 35% |
| 9 | Cy$_2$(o-Ph-Ph)P | | | 32% | 22% | 60:40 | 54% |
| 10 [f] | Cy$_2$FcP | | | 14% | 2% | 88:12 | 16% |

[a] Standard procedure: Ni(cod)$_2$ (20 mol%) and a ligand (40 mol %) were dissolved in 1.5 mL of toluene. Alkene (500 mol %), triethylamine (600 mol %), the aldehyde (100 mol %, 0.25 mmol), and Et$_3$SiOTf (175 (mol %) were added. The reaction mixture was stirred for 18 hours at 23 °C. [c] Yield determined by $^1$H NMR using DMF as a standard. [d] Ratio was determined by $^1$H NMR of the crude reaction mixture. [e] 48 h reaction time. [f] 1250 mol % alkene was used.

FIGURE 5

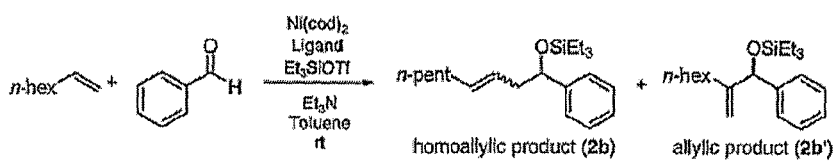

| entry | ligand | cone angle | $v_{CO}$ | combined yield [c] (2b+2b') | ratio (2b:2b') [d] | E:Z (2b) [d] |
|---|---|---|---|---|---|---|
| 1 [e] | Cy$_2$PhP | 162 | 1917 | 73 | 29:71 | n.d. |
| 2 | CyPh$_2$P | 153 | 1917 | 84 | 75:25 | 91:9 |
| 3 | (o-anisyl)$_3$P | 194 | 1919 | 70 | 83:17 | 80:20 |
| 4 | FcPh$_2$P | 173 | | 70 | 88:12 | 81:19 |
| 5 | (p-tol)$_3$P | 145 | 1920 | 78 | 92:8 | 67:33 |
| 6 | Ph$_3$P | 145 | 1922 | 73 | 92:8 | 67:33 |
| 7 | (p-F-Ph)$_3$P | 145 | 1924 | 74 | 92:8 | 57:43 |
| 8 | (p-CF$_3$-Ph)$_3$P | 145 | 1929 | 44 | >95:5 | 69:31 |
| 9 | (EtO)$_2$PhP | 121 | 1932 | 20 | >95:5 | 89:11 |
| 10 | (PhO)$_3$P | 128 | 1951 | <5 | n.d | n.d. |

[a] Standard procedure: Ni(cod)$_2$ (20 mol%) and a ligand (40 mol %) were dissolved in 2.5 mL of toluene. Alkene (1 mL), triethylamine (600 mol %), the aldehyde (100 mol %, 0.5 mmol), and Et$_3$SiOTf (175 mol %) were added. The reaction mixture was stirred for 18 hours at 23 °C. [c] Yield determined by $^1$H NMR using DMF as a standard. [d] Ratio was determined by $^1$H NMR after the products were treated with TBAF. [e] 48 h reaction time.

FIGURE 6

$H_2C=CH_2$ + PhCHO →[Ni(cod)$_2$, (o-anisyl)$_3$P, TESOTf / Et$_3$N, Toluene, rt] PhCH(OSiEt$_3$)CH=CH$_2$ (1a)

| entry | base | yield[b] |
|---|---|---|
| 1 | Et$_3$N | 77 |
| 2 | Et$_2$NH | 3 |
| 3 | N-methylpyrrolidine | 36 |
| 4 | proton sponge | 10 |
| 5 | pyridine | 12 |
| 6[c] | K$_3$PO$_4$ | <5 |
| 7 | K$_2$CO$_3$ | <5 |
| 8 | Cs$_2$CO$_3$ | <5 |

[a] Standard procedure: Ni(cod)$_2$ (20 mol %) and (o-anisyl)$_3$P (40 mol %) were dissolved in 2.5 mL of toluene under argon. Ethylene (balloon, 1 atm) was substituted for argon. A base (600 mol %), benzaldehyde (100 mol %, 0.5 mmol), and Et$_3$SiOTf (175 mol %) were added. The reaction mixture was stirred for 18 h at 23 °C. [b] Yields were determined by $^1$H NMR using DMF as a standard. [c] Benzaldehyde was replaced by 2-naphthaldehyde, and the reaction was run at 0.25 mmol scale.

FIGURE 7

| entry | base | combined yield (2b'+2b)[b] | ratio (2b':2b)[c] |
|---|---|---|---|
| 1 | Et₃N | 61% | 78:22 |
| 2 | Et(i-Pr)₂N | 10% | 60:40 |
| 3 | Cy₂NMe | 20% | 60:40 |
| 4 | N-methylpyrrolidine | 7% | 71:29 |
| 5 | 2,6-lutadine | 12% | 58:42 |

[a] Standard procedure: The nickel precatalyst system (20 mol %) was dissolved in 2.5 mL toluene. The alkene (1 mL), triethylamine (600 mol %), the aldehyde (100 mol %, 0.5 mmol), and Et₃SiOTf (175 mol %) were added. The reaction mixture was stirred for 48 hours at 23 °C. [b] Yields were determined by $^1$H NMR using DMF as a standard. [c] Ratios was determined by $^1$H NMR of the crude reaction mixture

*a* Standard procedure: The nickel precatalyst system (20 mol %) was dissolved in toluene. The alkene (500 mol %), triethylamine (600 mol %), the aldehyde (100 mol %), and Et₃SiOTf (175 mol %) were added. The reaction mixture was stirred for 48 hours at 23 °C. *b* Yields were determined by ¹H NMR using DMF as a standard.
*c* Ratios was determined by ¹H NMR of the crude reaction mixture. *d* 1 ml of 1-octene was used.

FIGURE 9

R¹-CH=CH₂ + R²CHO + R₃SiOTf → (Ni(cod)₂, Cy₂PhP, Et₃N, Toluene, rt) → allylic product (2') + homoallylic product (2)

| entry | R¹ (alkene) | R² (aldehyde) | R₃SiOTf | major product | | yield (%)[b] (2+2') | ratio (2':2)[c] |
|---|---|---|---|---|---|---|---|
| 1[d] | Me | naphthyl | Et₃SiOTf | [Me-C(=CH₂)-CH(OSiEt₃)-naphthyl] | 2r' | 82 | 84:16 |
| 2 | n-hexyl | Ph | Et₃SiOTf | [Me-(CH₂)₅-C(=CH₂)-CH(OSiEt₃)-Ph] | 2b' | 70 | 71:29 |
| 3[d] | Me | p-anisyl | Et₃SiOTf | [Me-C(=CH₂)-CH(OSiEt₃)-C₆H₄-OMe] | 2s' | 95 | 82:18 |
| 4 | Ph | N-methylindol-2-yl | Et₃SiOTf | [PhCH₂-C(=CH₂)-CH(OSiEt₃)-(N-Me-indolyl)] | 2k' | 56[e] | 80:20 |
| 5 | isobutyl | Ph | Et₃SiOTf | [Me₂CH-CH₂-C(=CH₂)-CH(OSiEt₃)-Ph] | 2n' | 62 | 71:29 |
| 6 | Me₂C=CH-CH₂-CH₂-CH=CH₂ | Ph | Et₃SiOTf | [Me₂C=CH-(CH₂)₂-C(=CH₂)-CH(OSiEt₃)-Ph] | 2t' | 72 | 71:29 |
| 7 | c-hexyl | Ph | Et₃SiOTf | [cyclohexyl-C(=CH₂)-CH(OSiEt₃)-Ph] | 2p' | 5[f] | n.d. |

[a] Standard procedure: Ni(cod)₂ (20 mol%) and Cy₂PhP (40 mol %) were dissolved in 2.5 mL of toluene. Excess alkene, triethylamine (600 mol %), the aldehyde (100 mol %, 0.5 mmol), and Et₃SiOTf (175 mol %) were added. The reaction mixture was stirred for 18 hours at 23 °C. [b] Unless specified, isolated yield of all coupling products. [c] Ratios were determined by $^1$H NMR of the crude reaction mixture. [d] 1 atm of propene (balloon) was used, and naphthaldehyde (100 mol%) was mixed with Ni(cod)₂ and Cy₂PhP before the addition of toluene. [e] Yields were determined by $^1$H NMR using DMF as a standard. [f] Isolated yield of the allylic product 2p'.

FIGURE 10

| entry | R¹ (alkene) | R² (aldehyde) | ligand | major product | | yield (%)[b] | ratio (4:4')[b] | ratio (E:Z)[c] |
|---|---|---|---|---|---|---|---|---|
| 1 | (phthalimide-CH₂-CH=CH₂) | Ph | Cy₂PhP | (phthalimide-CH₂-C(=CH₂)-CH(OSiEt₃)Ph) | 4a | 67 | 74:26 | |
| 2 | (phthalimide-CH₂-C(CH₃)₂-CH=CH₂) | o-anisyl | Cy₂PhP | (phthalimide-CH₂-CH₂-C(=CH₂)-CH(OSiEt₃)(C₆H₄OMe)) | 4b | 54 | 71:29 | |
| 3 | (oxazolidinone-CH₂-C(CH₃)₂-CH=CH₂) | Ph | Cy₂PhP | (oxazolidinone-CH₂-CH₂-C(=CH₂)-CH(OSiEt₃)Ph) | 4c | 60 | 83:17 | |

[a] Standard procedure: To a solution of Ni(cod)₂ (0.1 mmol) and ligand (0.2 mmol) in toluene (2.5 mL) at 23 °C under Ar were added the alkene (1.5 mmol), triethylamine (3.0 mmol), the aldehyde (0.5 mmol), and Et₃SiOTf (0.875 mmol). The mixture was stirred for 48 h at room temperature and purified by chromatography (SiO₂). [b] Determined by ¹H NMR of the crude reaction mixture using DMF as a standard. [c] The ratio was determined by ¹H NMR of the mixture of E and Z homoallylic alcohols after the silyl group of the coupling product was removed by TBAF.

FIGURE 11

| entry | R¹ (alkene) | R² (aldehyde) | ligand | major product | yield (%)[b] | ratio (4:4')[b] | ratio (E:Z)[c] |
|---|---|---|---|---|---|---|---|
| 1 | PhC(O)OCH₂CH=CH₂ (benzoate allyl) | Ph | Cy₂PhP | benzoate-CH₂-C(=CH₂)-CH(OSiEt₃)Ph | 4d | <5 | n.d. |
| 2[e] | PhC(O)OCH₂CH₂CH=CH₂ | Ph | Cy₂PhP | benzoate-CH₂CH₂-C(=CH₂)-CH(OSiEt₃)Ph | 4e | 21 | n.d. |
| 3 | Ph-C(O)-O-(CH₂)₃-CH=CH₂ | o-anisyl | Cy₂PhP | Ph-C(O)-O-(CH₂)₄-C(=CH₂)-CH(OSiMe₂t-Bu)(p-OMe-C₆H₄) | 4f | 44[d] | 73:27 |

[a] Standard procedure: To a solution of Ni(cod)₂ (0.1 mmol) and ligand (0.2 mmol) in toluene (2.5 mL) at 23 °C under Ar were added the alkene (2.5 mmol), triethylamine (3.0 mmol), the aldehyde (0.5 mmol), and Et₃SiOTf (0.875 mmol). The mixture was stirred for 48 h at room temperature and purified by chromatography (SiO₂). [b] Determined by ¹H NMR of the crude reaction mixture using DMF as a standard. [c] The ratio was determined by ¹H NMR of the mixture of E and Z homoallylic alcohols after the silyl group of the coupling product was removed by TBAF. [d] Isolated yield. [e] 1.5 mmol of alkene were used.

CATALYTIC REACTIONS INVOLVING ALKENES

STATEMENT REGARDING FEDERALLY SPONSORED RESEARCH OR DEVELOPMENT

This invention was made with government support under Grant Number 5-R01-GM-63755-05 awarded by the National Institute of Health. The government has certain rights in this invention.

FIELD OF THE INVENTION

The present invention relates to compositions and methods involving catalytic coupling reactions between alkenes and aldehydes.

BACKGROUND OF THE INVENTION

Aliphatic terminal alkenes (or alpha-olefins) are produced in metric megaton amounts each year, and these chemical feedstocks are starting materials for the preparation of many classes of organic compounds. The value-added component of catalytic intermolecular reactions of these alkenes, such as Ziegler-Natta oligomerization, the Heck reaction, and cross-metathesis, is especially high because they convert an inexpensive raw material into a more highly functionalized compound or polymer with concomitant formation of one or more carbon-carbon bonds.

Allylic alcohols are important building blocks commonly used in the synthesis of natural products and other complex molecules and polymers. However, current synthetic methods known to the inventors have not been able to incorporate alpha-olefins in the synthesis of allylic alcohols. Previous studies typically have involved metal-catalyzed, intermolecular reductive coupling reactions of aldehydes with alkynes, 1,3-dienes, allenes, enoate esters, enones, and enals. In these examples, a reactive π-bond has been, in effect, converted to an anion equivalent by a reductive process. Because the less reactive π-bond of an alpha-olefin may not as easily be activated in this manner, catalytic intermolecular coupling (e.g., reductive or otherwise) of these alkenes and aldehydes has not been achieved. While catalytic carbonyl-ene reactions between alpha-olefins and aldehydes provide homoallylic alcohols, there is no method known to the inventors for joining these two building blocks to provide allylic alcohols. Nickel-promoted, intramolecular alkene-aldehyde reductive coupling was recently described (Ogoshi, S.; Oka, M.-a.; Kurosawa, H. *J. Am. Chem. Soc.* 2004, 126, 11802-11803), but this process required a stoichiometric amount of nickel and was not effective in intermolecular cases.

Accordingly, improved methods are needed.

SUMMARY OF THE INVENTION

The present invention relates to methods comprising reacting an alkene and an aldehyde to form an allylic alcohol or precursor of an allylic alcohol, provided that the aldehyde is not formaldehyde.

The present invention also relates to methods comprising reacting an alkene and an aldehyde to form an allylic alcohol or precursor of an allylic alcohol, provided that the alkene is not an electron deficient alkene.

Also, the present invention provides methods comprising reacting an alkene and an aldehyde in the presence of a catalyst to form an allylic alcohol or precursor of an allylic alcohol, wherein the catalyst is a compound comprising a Group 9, Group 10, or Group 11 metal.

The present invention further provides methods comprising reacting three components in the presence of a catalyst to form an allylic alcohol or precursor of an allylic alcohol, wherein the catalyst is a compound comprising a Group 9, Group 10, or Group 11 metal, and wherein one of the three components is an alpha-olefin.

The present invention also relates to compositions of matter comprising a nickel-containing compound, a phosphorus-containing agent having the ability to ligate the nickel, a silicon-containing compound, and a base, wherein the phosphorus-containing ligand is dicyclohexylphenylphosphine or tri(ortho-anisyl)phosphine.

The present invention also relates to compositions useful for promoting reaction between catalyst system for coupling an alpha-olefin and an aldehyde to form an allylic alcohol or precursor of an allylic alcohol, comprising a nickel-containing compound, a phosphorus-containing ligand, a silicon-containing compound, and a base.

BRIEF DESCRIPTION OF THE DRAWINGS

FIG. 1B lists examples of nickel-catalyzed formation of silyl ethers of allylic alcohols from alpha-olefins and aldehydes, in accordance with the invention.

FIG. 4 lists examples of nickel-catalyzed formation of silyl ethers of allylic alcohols in the presence of electron-rich phosphines.

FIG. 5 lists examples of nickel-catalyzed formation of silyl ethers of allylic alcohols in the presence of electron-poor phosphines.

FIG. 6 lists examples of a nickel-catalyzed coupling of ethylene and benzaldehyde in the presence of various bases.

FIG. 7 lists examples of a nickel-catalyzed coupling of 1-octene and benzaldehyde in the presence of various bases.

FIG. 9 lists examples of nickel-catalyzed formation of silyl ethers of allylic alcohols from substituted alpha-olefins and aldehydes, in accordance with the invention.

FIG. 10 lists examples of nickel-catalyzed coupling of nitrogen-containing alkenes with aldehydes.

FIG. 11 lists examples of nickel-catalyzed coupling of oxygen-containing alkenes with aldehydes.

DETAILED DESCRIPTION

Figure 1A:
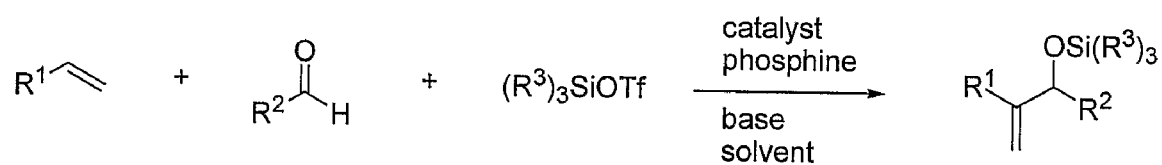
FIG. 1A shows the nickel-catalyzed formation of silyl ethers of allylic alcohols from alpha-olefins and aldehydes, in accordance with the invention.

The present invention relates to new compositions and reactions to produce allylic alcohols or precursors of allylic alcohols (e.g., silyl ethers of allylic alcohols). Methods of the invention may comprise combining an alkene and an aldehyde in the presence of a transition metal catalyst (e.g., a nickel catalyst) to form an allylic alcohol or precursor of an allylic alcohol. Reaction products of the present invention may be valuable as intermediates and/or products in pharmaceutical and polymer research. Also, methods of the invention may be useful as fragment coupling reactions in complex molecule synthesis. Moreover, methods of the invention may include the use of reagents which, under reaction conditions known in the art, may have been unreactive, i.e., may not have been able to form the reaction product. The reagents used in the present invention may be relatively lower in cost than in other methods. Also, methods of the invention may reduce the number of synthetic and purification steps required to produce the reaction products, as well as reducing time, cost, and waste production.

In one set of embodiments, methods of the present invention may be used to catalytically couple an alkene and an aldehyde to form an allylic alcohols or precursor of an allylic alcohol, such as a silyl ether of an allylic alcohol. As used herein, the term "precursor" refers to compound which may be converted to a final product (e.g., an allylic alcohol) by one chemical reaction, such as a deprotection. For example, precursors of allylic alcohols may include silyl ethers of allylic alcohols and other protected allylic alcohols. The method may further comprise a silicon (Si) compound, a phosphine, a base, and/or a solvent. The present invention may be particularly advantageous for less reactive alkenes, such as alpha-olefins, as further described below. The present invention further provides methods comprising at least reacting three components all contained together in a single reaction chamber in the presence of a catalyst to form an allylic alcohol or precursor of an allylic alcohol, wherein the catalyst is a compound comprising a Group 9, Group 10, or Group 11 metal, and wherein one of the three components is an alpha-olefin. In some embodiments, one of the three components is an aldehyde. In some embodiments, one of the three components is a Si compound. In a particular embodiment, the three components are an alpha-olefin, an aldehyde, and a Si compound. That is, the present invention may involve an (at least) three component, one-pot synthesis of allylic alcohols and silyl ethers thereof. The term "one-pot" reaction is known in the art and refers to a chemical reaction which can produce a product in one step which may otherwise have required a multiple-step synthesis. One-pot procedures may eliminate the need for isolation (e.g., purification) of intermediates and additional synthetic steps while reducing the production of waste materials (e.g., solvents, impurities). Additionally, the time and cost required to synthesize such compounds are reduced.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s). A "stable, isolable compound" refers to isolated reaction products and does not refer to unstable intermediates or transition states.

Embodiments of the invention may comprise the reductive coupling of aldehydes and alkenes. The term "reductive coupling" is known in the art and may be defined, for example, in L. S. Hegedus, Organometallics in Synthesis, M. Schlosser, Ed., Wiley, 1994. In some cases, embodiments of the invention may also comprise non-reductive coupling of aldehydes and alkenes.

Scheme 1 and FIG. 1A show an illustrative embodiment of the invention, wherein, in the presence of a catalyst and a silyl triflate, an alkene (for example, an alpha-olefin) can be coupled with an aldehyde to form a silyl ether of an allylic alcohol, in nearly quantitative yield in some cases. In the present invention, the alkene may be considered a functional equivalent of a 2-alkenylmetal reagent that may be added to the electrophilic carbon of an aldehyde, complementary to a 1-alkenylmetal reagent in addition reactions to aldehydes. In one embodiment, the reaction (e.g., coupling of alkene and aldehyde) may be intermolecular. That is, the alkene and the aldehyde are not joined by a bond prior to the coupling reaction. In another embodiment, the reaction may be intramolecular. In another embodiment, the alkene-aldehyde coupling occurs in the presence of certain phosphine ligands, a silyl triflate, and a base, such as an amine base.

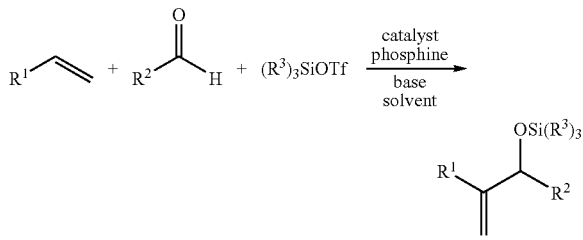

Scheme 1

FIG. 1B lists embodiments of methods of the present invention (Entries 1-14). Alkenes, aldehydes, and silyl triflates may undergo nickel-catalyzed coupling under relatively mild conditions (1 atm $H_2C=CH_2$, room temperature), yielding silyl ethers of allylic alcohols. In some cases, the isolated yield of the product is nearly quantitative (entries 3-5, FIG. 1), highlighting the efficient assembly of protected allylic alcohols in a single operation using methods of the present invention. In some embodiments, methods of the invention are tolerant of sterically demanding aliphatic aldehydes, such as pivaldehyde and 2,2-dimethyl-3-oxo-propionic acid methyl ester (entries 12 and 13, FIG. 1). In some embodiments, methods of the invention demonstrate compatibility with additional functional groups on the alkene and/or the aldehyde, as described more fully below. For example, the coupling reaction may proceed in the presence of ortho-substitution on an aromatic aldehyde (entry 3, FIG. 1), acid-sensitive heteraromatic aldehydes (entries 8-9, FIG. 1), or an ester substitution on the aldehyde (entry 13, FIG. 1). In some cases, enolizable aldehydes may be used in methods of the invention (entry 14, FIG. 1).

Figure 2:
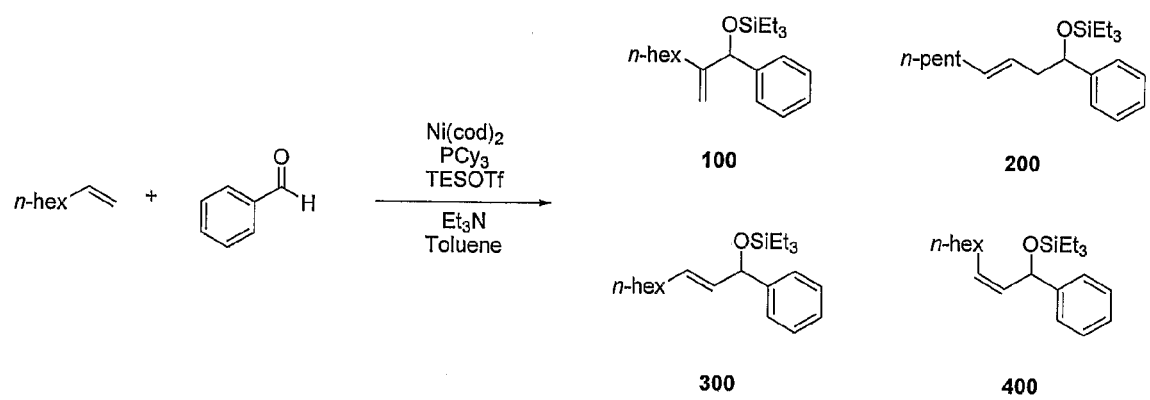
FIG. 2 shows the possible products formed by the inventive nickel-catalyzed reductive coupling of 1-octene, benzaldehyde, and ethylsilyltriflate.

In some embodiments, reaction products other than allylic alcohols or silyl ethers of allylic alcohols may be obtained. For example, coupling reactions with monosubstituted alkenes may produce additional reaction products. One of the reaction products observed in these reactions may be the isomeric homoallylic alcohol derivative. For example, FIG. 2 shows the products formed by the reaction of 1-octene with benzaldehyde in the presence of triethylsilyl triflate. The major product is allylic alcohol 100, while the minor product is homoallylic alcohol 200. Compounds 300 and 400 are formed in trace amounts, such as less than 1% or not at all. Remarkably, in substantially all embodiments, only one (100) of the three possible allylic alcohol derivatives (100, 300, and 400) may be formed in greater than 1% yield in the reaction.

One possible explanation for this product distribution may be that one of the key intermediates in the reaction mechanism is an oxametallacycle (e.g., oxanickellacycle) having the structures,

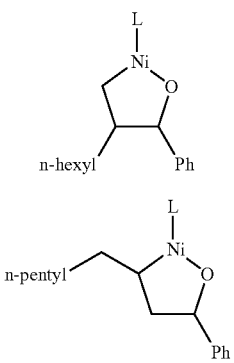

Oxametallacycle A may lead to the observed allylic product (100) by reaction with the silyl triflate, cleavage of the Ni—O bond, and then β-H elimination. Alternatively, β-H elimination directly from oxametallacycle A would also form allylic alcohol 100. However, it may be unlikely since the transition state required would be highly strained. This notion may also be supported by the fact that allylic alcohol products 300 and 400, which would result from the corresponding β-H elimination from oxametallacycle B, are generally not formed in the reaction. The homoallylic alcohol product (200) may be explained by oxametallacycle B. With the alkyl chain of the olefin adjacent to the Ni center, the transition state for β-H elimination directly from oxametallacycle B may be less strained than those from oxametallacycle A and oxametallacycle B that would lead to allylic alcohol products. Another possibility is that, as in the case of oxametallacycle A, oxametallacycle B first reacts with the silyl triflate. Subsequent β-H elimination toward the newly installed carbinol center, which would lead to the generally unobserved allylic alcohol derivatives 3 and 4, might thus be disfavored for steric and/or electronic reasons.

Figure 12:
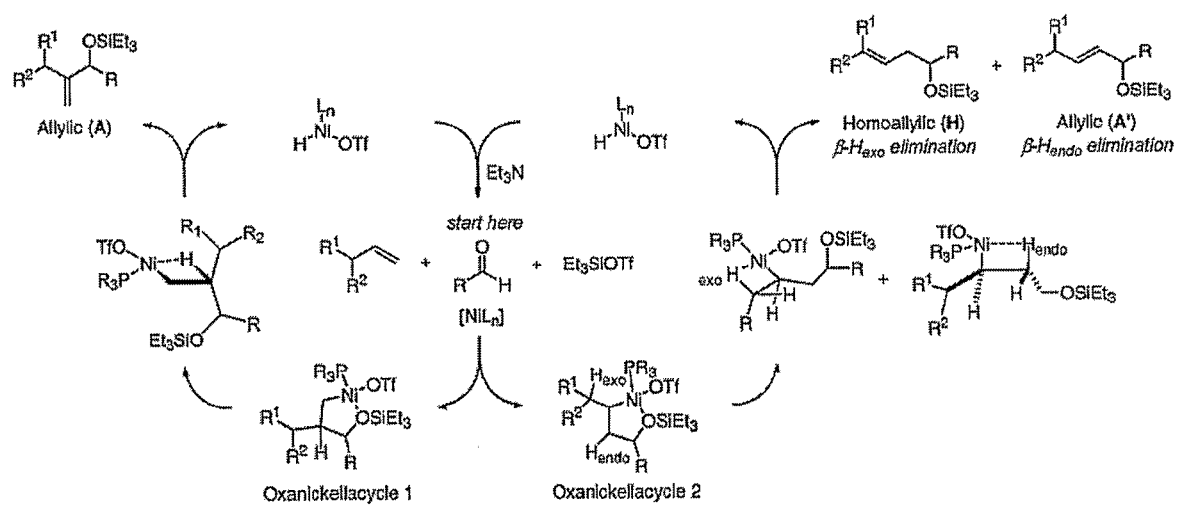
FIG. 12 shows a schematic illustration of a proposed reaction mechanism for nickel-catalyzed formation of silyl ethers of allylic alcohols from alpha-olefins and aldehydes.

Without wishing to be bound by theory, FIG. 12 shows a proposed reaction mechanism for nickel-catalyzed coupling of alpha-olefins and aldehydes. The coupling reaction may proceed through the formation of an oxanickellacycle from a nickel(0) complex (FIG. 12), and a syn beta-hydride elimination may afford the coupling product and a nickel-hydride species, analogous to a Heck reaction. Subsequent base-promoted reductive elimination of the nickel hydride intermediate may regenerate the nickel(0) catalyst. In some cases, base-mediated beta-elimination of the oxanickellacycle via an E2-like mechanism may occur. By modifying reaction conditions such as metal catalyst, phosphine ligand, base, solvent, reaction temperature, and the like, the product distribution may be varied to suit a particular desired result, as described more fully below. For example, the phosphorus-containing compound (e.g., phosphine ligand) may be selected to favor formation of the allylic product over the homoallylic product.

Conceptually, in the methods presented here, an alkene functions as an alkenylmetal reagent that is added to an aldehyde. However, compared to known, organometallic reagents, the alkene in this unprecedented bond construction has important advantages, such as greater off-the-shelf availability and greater functional group compatibility. Methods of the invention may also be employed in enantioselective reactions to form chiral allylic alcohols, by employing chiral moieties on the catalyst ligands, phosphines, bases, solvents, and/or the like. Those of ordinary skill in the art would be able to conduct such experiments in order to find the optimal reaction conditions to suit a particular, desired result.

The present invention also relates to compositions of matter comprising a nickel-containing compound, a phosphorus-containing agent having the ability to ligate the nickel, a silicon-containing compound, and a base. In some cases, the composition may be useful for promoting reaction between catalyst system for coupling an alpha-olefin and an aldehyde to form an allylic alcohol or precursor of an allylic alcohol. In some cases, the phosphorus-containing ligand is dicyclohexylphenylphosphine or tri(ortho-anisyl)phosphine. In some embodiments, the alkene has the structure,

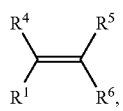

wherein $R^1$, $R^4$, $R^5$, and $R^6$ can be independently hydrogen, optionally substituted alkyl, optionally substituted cycloalkyl, optionally substituted aralkyl, optionally substituted heteroaralkyl, optionally substituted alkenylalkyl, or optionally substituted alkynylalkyl.

In certain embodiments, the alkene is an alpha-olefin having the structure,

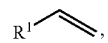

wherein $R^1$ can be optionally substituted alkyl, optionally substituted cycloalkyl, optionally substituted aralkyl, optionally substituted heteroaralkyl, optionally substituted alkenylalkyl, or optionally substituted allynylalkyl. As used herein, the terms "olefin" and "alkene" can be used interchangeably to describe a carbon-carbon double bond. The term "alpha-olefin" is known in the art and refers to an olefin positioned at the alpha or 1-position, i.e. between two terminal carbons of a carbon chain.

Examples of alkenes that may be used in the present invention include, but are not limited to, ethylene, monosubstituted olefins (e.g., alpha-olefins) such as 1-propene, 1-butene, 1-pentene, 1-hexene, 1-heptene, 1-octene, 1-nonene, 1-decene, 4-methyl-1-pentene, substituted derivatives thereof, more highly substituted alkenes (e.g., di-substituted, tri-substituted, etc.), and the like. Methods of the invention may also proceed with tolerance of additional functional groups on the alkene. That is, reaction of the alkene may proceed in the presence of other functional groups without substantial decrease in the reaction performance and with retention of the functional group. For example, in one embodiment, the reaction proceeds with an alkene containing both an alpha-olefin functionality and a tri-substituted olefin, with coupling only occurring at the alpha-olefin, as shown in entry 6 of FIG. 9.

Methods of the invention may advantageously allow for the reaction of alkenes (e.g., alpha-olefins) which have relatively less reactive pi-bonds than other substituted olefins. For example, "electron-deficient" alkenes such as enones, enoate esters, enals, vinyl sulfonyls and sulfones, or other alkenes positioned adjacent to an electron-deficient group may have increased reactivity. As used herein, an "electron-deficient" alkene refers to an alkene positioned adjacent to an electron-withdrawing group. The term "electron-withdrawing" group is known in the art and as used herein refers a functionality which draws electrons to itself more than a hydrogen atom would at the same position. Examples of electron-withdrawing groups include, but are not limited to, nitro, carbonyl groups such as ketone, aldehyde, or ester, sulfone, sulfonyl, trifluoromethyl, cyano, functional groups comprising a relatively highly electrophilic atom, and the like. Methods of the invention are particularly advantageous for relatively less reactive olefins, such as alpha-olefins. In certain embodiments, alkenes which may not be able to react to form allylic alcohols using other reaction conditions known in the art may readily react using methods of the present invention.

In some embodiments, the alkene is present in less than or equal to about 2000 mol % relative to the aldehyde. In some embodiments, the alkene is present in less than or equal to about 1500 mol % relative to the aldehyde. In some embodiments, the alkene is present in less than or equal to about 1000 mol % relative to the aldehyde. In some embodiments, the alkene is present in less than or equal to about 500 mol % relative to the aldehyde. In one embodiment where the alkene is ethylene, a pressure of 1 atm ethylene gas is maintained.

Certain screening tests may be employed to determine which alkenes may be preferred for use in methods of the present invention. For example, in some embodiments, alkenes which are substituted with at least one hydrogen are preferred, in order to permit β-H-elimination of the metal catalyst to afford the final reaction product. In some cases, ethylene and monosubstituted alkenes may be preferred for use in the nickel-catalyzed coupling reaction, while 1,1-disubstituted alkenes, acyclic 1,2-disubstituted (cis or trans) alkenes, and trisubstituted alkenes may be less reactive. However, since methods of the invention can easily be carried out and require relatively short reaction times, a wide ranges of alkenes may be tested simply by subjecting them to reaction methods described herein. The scope of alkenes suitable for use in the present invention is discussed more fully below.

Some embodiments of the invention comprise the use of aldehydes having the structure,

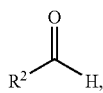

wherein $R^2$ can be optionally substituted alkyl, optionally substituted cycloalkyl, optionally substituted aryl, optionally substituted heteroaryl, optionally substituted aralkyl, optionally substituted heteroaralkyl, optionally substituted alkenylalkyl, or optionally substituted alkynylalkyl. Examples of suitable aldehydes include, but are not limited to, benzaldehyde, tolualdehyde, anisaldehyde, napthaldehyde, furaldehyde, acetaldehyde, propionaldehyde, butylaldehyde, hexylaldehyde and benzaldehyde, other carboxaldehydes, and the like. The term "aldehyde" is known in the art and refers to a group having the formula, C(=O)H.

In some embodiments, methods of the present invention are useful for sterically demanding aliphatic aldehydes, i.e., aldehydes having highly substituted and/or bulky substituents. Aldehydes which have sterically bulky substituents positioned adjacent to the electrophilic carbonyl may typically experience decreased reactivity due to the inaccessibility of the electrophilic carbon. However, in the present invention, sterically bulky aldehydes, such as pivaldehyde and other tertiary aldehydes, may undergo smooth coupling to provide the reaction product.

In other embodiments, methods of the present invention are compatible with aldehydes substituted with additional functional groups, as described herein.

In the case where $R^2$ is hydrogen, the aldehyde is formaldehyde, which is generally more reactive relative to other aldehydes in that the carbon of formaldehyde is relatively more electrophilic. That is, substitution at the carbonyl by, for example, an alkyl or aryl group may stabilize the carbonyl, making it relatively less reactive than formaldehyde. While known methods may be employed using formaldehyde as the aldehyde, such methods may not be successful using less reactive, substituted aldehydes. Methods of the present invention may be suited for cases wherein $R^2$ is not H, wherein the reactivity of the aldehyde is relatively lower.

In some embodiments, the aldehyde is the limiting reagent in the reaction.

Screening tests may be employed to determine which aldehydes may be preferred for use in methods of the present invention, including subjecting an aldehyde to the reaction conditions described herein. Methods of the invention can easily be carried out and require relatively short reaction times, allowing a wide ranges of aldehydes to be tested. For example, in certain embodiments, the use of an aliphatic aldehyde bearing at least one hydrogen adjacent to the carbonyl may not be preferred due to the potential for a competing side reaction to occur, wherein enolization of the aldehyde takes place. In some cases, the aldehyde may be preferably be an electron-rich aromatic aldehyde, wherein the aromatic ring is substituted with electron-donating substituents (e.g, methyl, methoxy), as shown by entries 2 and 4 of FIG. 1.

Figure 3:
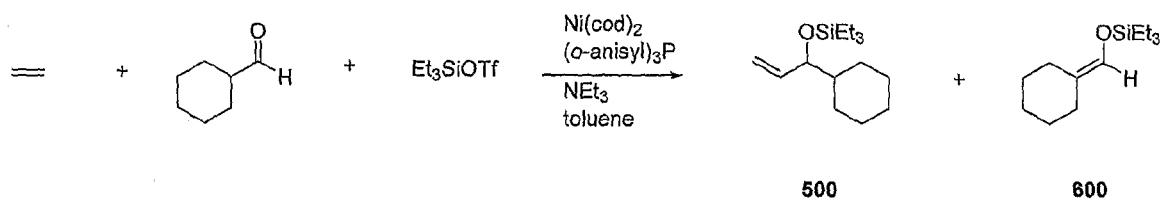
FIG. 3 shows the two products formed by the inventive nickel-catalyzed reductive coupling of ethylene, cyclohexanealdehyde, and ethylsilyltriflate.

As shown in FIG. 3, the coupling of ethylene with cyclohexanecarboxaldehyde using the reaction conditions described herein results in the formation of both the silyl ether of the allylic alcohol 500 and the silylenolether of cyclohexanecarboxaldehyde 600, with a product ratio of about 2:1 favoring the silyl ether 500.

The "transition metal catalyst" of the present invention, as used herein, may include any catalytic transition metal and/or catalyst precursor as it is introduced into the reaction vessel and which may be, if needed, converted in situ into the active form, as well as the active form of the catalyst which participates in the reaction. In some embodiments, the transition metal catalyst is provided in the reaction mixture in a catalytic amount. In certain embodiments, that amount is in the range of 0.01 to 40 mol %, and preferably 10 to 30 mol %, and most preferably 20-25 mol %, with respect to the limiting reagent, which may be either the aldehyde, the alkene, the silyl triflate compound, or all three components, depending upon which reagent is in stoichiometric excess. In some embodiments, the catalyst is present in less than or equal to about 40 mol % relative to the aldehyde. In some embodiments, the catalyst is present in less than or equal to about 30 mol % relative to the aldehyde. In some embodiments, the catalyst is present in less than or equal to about 20 mol % relative to the aldehyde. In the case where the molecular formula of the catalyst complex includes more than one metal, the amount of the catalyst complex used in the reaction may be adjusted accordingly.

As suitable, the catalysts employed in the present invention may involve the use of metals which can mediate reductive coupling of the alkenes and aldehydes as defined above. In general, any transition metal (e.g., having d electrons) may be used to form the catalyst, e.g., a metal selected from one of Groups 3-12 of the periodic table or from the lanthanide series. However, in preferred embodiments, the metal will be selected from Groups 8-12, more preferably Groups 9-11, and even more preferably Group 10. According to the conventions used herein, the term "Group 9" refers to the transition metal group comprising cobalt, rhodium, and iridium, the term "Group 10" refers to the transition metal group comprising nickel, palladium, and platinum, etc. For example, suitable metals include, but are not limited to, cobalt, rhodium, iridium, nickel, palladium, platinum, copper, silver, or gold, more preferably nickel, palladium, or platinum. It is expected that these catalysts will perform similarly because they are known to undergo similar reactions which are thought to be involved in the formation of the reaction products of the present invention, such as formation of an oxametallacycle. However, the different ligands are thought to modify the catalyst performance by, for example, modifying reactivity and preventing undesirable side reactions. In a particular embodiment, the catalyst comprises nickel or a nickel-containing compound. Additionally, heterogeneous catalysts containing forms of these elements are also suitable catalysts for any of the transition metal catalyzed reactions of the present invention.

The particular form of the metal to be used in the reaction is selected to provide, under the reaction conditions, metal centers which are coordinately unsaturated and not in their highest oxidation state. In some embodiments, a zero-valent metal center ($M^0$) may be thought to participate in the catalytic carbon-carbon bond forming sequence by formation of an oxametallacycle with the aldehyde and alkene. Thus, the metal center may be desirably in the zero-valent state. The zero-valent nickel compounds may be prepared or generated according to techniques well known in the art, as described, for example, in U.S. Pat. Nos. 3,496,217; 3,631,191; 3,846,461; 3,847,959; and 3,903,120, which are incorporated herein by reference. In some cases, zero-valent nickel compounds comprising ligands which can be displaced by other ligands (e.g., organophosphorus ligands) may be a preferred source of zero-valent nickel.

Alternatively, the metal center may be capable of being reduced to the zero-valent state by, for example, in situ reduction from an $M^{+2}$ species. Divalent nickel compounds ($Ni^{+2}$) may be combined with a reducing agent to serve as a source of zero-valent nickel in the reaction. Suitable reducing agents include metal borohydrides, metal aluminum hydrides, metal alkyls, Zn, Fe, Al, Na, or $H_2$. For example, $Ni(acac)_2$ may also be used with the addition of $(i-Bu)_2AlH$ (DIBAL-H) to produce the zero-valent nickel. The nickel portion of the catalyst may be finely divided nickel metal (alone or on a support such as carbon or alumina) or a nickel compound which is or becomes soluble in the reaction medium.

Suitable nickel compounds include, but are not limited to, $Ni(cod)_2$ (cod=1,5-cyclooctadiene), $Ni(acetate)_2$, $Ni(Ph_3P)_4$, nickel carboxylates, nickel propionates, nickel halides such as $NiBr_2$, $NiCl_2$, $Ni(Ph_3P)_2Cl_2$, $Ni(Ph_3P)_2Br_2$, $NiF_2$, and $NiI_2$, nickel cyanide, nickel nitrate, nickel sulfide, nickel sulfite, nickel sulfate, nickel oxalate, nickel phosphate, nickel stearate, nickel acetylacetonate, nickel tetrafluoroborate, nickel thiocyanate, nickel carbonate, nickel sulfamate, $Ni(1,10\text{-phenanthroline})_2$, $Ni(dppf)_2$ (dppf=1,1'-bis(diphenylphosphino)-ferrocine), and the like. In some cases, nickel acetylacetonate and $Ni(cod)_2$ may be used. In one particular embodiment, the nickel catalyst may preferably be $Ni(cod)_2$.

The coupling reaction can be also be catalyzed by palladium or platinum catalysts. Examples of such catalysts include, but are not limited to, inorganic salts of palladium or platinum including bromides, chlorides, fluorides, iodides, cyanides, nitrates, sulfides, sulfites, and sulfates, organic palladium or platinum complexes and salts such as carboxylates, e.g., acetates or propionates, $Pd(acetate)_2$, palladium(II) chloride, $Pd(CH_3CN)_4(BF_4)_2$, $PdCl_2(CH_3CN)_2$, $PdCl_2(PhCN)_2$, $PdCl_2(PPh_3)_2$, $PdCl_2$, $Pd(acetate)_2$, $(CH_3CN)_2PdCl_2$, $Pd(PPh_3)_4$, tris(dibenzylideneacetone)dipalladium (0), palladium trifluoroacetate, and corresponding platinum complexes thereof.

Ligands on the metal catalyst may include chelating ligands, such as alkyl and/or aryl derivatives of phosphines and/or bisphosphines, amines, diamines, imines, arsines, and hybrids thereof, including hybrids of phosphines with amines. Weakly or non-nucleophilic stabilizing ions are preferred to avoid complicating side reaction of the counter ion, for example, attacking or adding to the electrophilic center of the aldehyde. This catalyst complex may include additional ligands as is necessary to obtain a stable complex. Moreover, the ligand can be added to the reaction mixture in the form of a metal complex, or added as a separate reagent relative to the addition of the metal. The ligand, if chiral can be provided as a racemic mixture or a purified stereoisomer.

In some embodiments of the invention, one or more phosphorus-containing agents (e.g., phosphine ligands) capable of ligating the metal center (e.g., nickel) may be added, e.g., as a Lewis basic ligand that controls the stability and electron transfer properties of the transition metal catalyst, and/or stabilizes the metal intermediates. Phosphine ligands suitable for use in the present invention include those which are capable of binding to a metal catalyst during a coupling reaction, for example, to control the regioselectivity of the coupling reaction. In some cases, the use of sterically large, electron-donating phosphines may be desired for use in methods of the invention. Those of ordinary skill in the art would be able to select such phosphine ligands based on, for example, the sigma-electron-donating ability of a phosphine ligand, as described more fully below.

Phosphine ligands are commercially available or can be prepared by methods similar to processes known in the art. The phosphines can be monodentate phosphine ligands, such as trimethylphosphine, triethylphosphine, tripropylphosphine, triisopropylphosphine, tributylphosphine, trioctylphosphine, tricyclohexylphosphine, triphenylphosphine, dimethylphenylphosphine, dicyclohexylphenylphospine, dicyclohexyl-(o-tolyl)-phenylphospine, dicyclohexylbiphenyl-phosphine, dicyclohexylferrocenyl-phenylphospine, tricyclopentylphosphine, tri(o-tolyl)phosphine, tri(o-tolyl) phosphine, tri(o-anisyl)phosphine, neomenthyl-diphenylphosphine (NMDPP), trimethyl phosphite, triethyl phosphite, tripropyl phosphite, triisopropyl phosphite, tributyl phosphite, tricyclohexyl phosphite, and the like. In some embodiments, bis(phosphine) ligands may be added as supporting ligands. Suitable bis(phosphine) compounds include, but are not limited to, (±)-2,2'-bis(diphenylphosphino)-1,1'-binaphthyl (and separate enantiomers), (±)-2,2'-bis(di-p-tolylphosphino)-1,1'-binaphthyl (and separate enantiomers), 1-1'-bis(diphenylphosphino)ferrocene (dppf), 1,3-bis(diphenylphosphino)propane (dppp), 1,2-bis(diphenylphosphino) benzene, 2,2'-bis(diphenylphosphino)diphenyl ether, and 1,2-bis(diphenylphosphino)ethane (dppe). or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropyl-phosphino)ethane, 1,2-bis(diisopropylphosphino)ethane, 1,2-bis(dibutyl-phosphino)ethane, 1,2-bis(dicyclohexylphosphino) ethane, 1,3-bis(dicyclohexylphosphino)-propane, 1,3-bis(diiso-propylphosphino)propane, 1,4-bis(diisopropylphosphino)-butane, 2,4-bis(dicyclohexylphosphino)pentane, and the like. Hybrid chelating ligands such as (±)-N,N-dimethyl-1-[2-(diphenylphosphino) ferrocenyl]ethylamine (and separate enantiomers), and (±)-

(R)-1-[(S)-2-(diphenylphosphino)-ferrocenyl]ethyl methyl ether (and separate enantiomers) are also within the scope of the invention.

In some cases, triphenylphosphine, tricyclopentylphosphine, tricyclohexylphosphine, triisopropylphosphine, (2-biphenyl)dicyclohexylphosphine, dicyclohexylphenylphospine, dimethylphenylphosphine, tributylphosphine, trioctylphosphine, tri(o-anisyl)phosphine, NMDPP are preferred. In particular embodiments, tri(o-anisyl)phosphine or dicyclohexylphenylphospine are preferred.

In some embodiments, the phosphine is present in less than or equal to about 60 mol % relative to the aldehyde. In some embodiments, the phosphine is present in less than or equal to about 50 mol % relative to the aldehyde. In some embodiments, the phosphine is present in less than or equal to about 40 mol % relative to the aldehyde.

In some instances, it may be necessary to include additional reagents in the reaction to promote reactivity of, for example, the transition metal catalyst or other components of the reaction. In particular, it may be advantageous to include a suitable base. Bases suitable for use in the invention include those having sufficient pKa values (e.g., greater than 5) to deprotonate the metal catalyst upon β-H elimination. The base may also be selected to have appropriate nucleophilicity and/or steric bulk to effectively promote the coupling reaction, as known to those of ordinary skill in the art. For example, it may be preferable to employ bases which do not compete with the phosphorus ligand, alkene, and/or aldehyde for a coordination site on the metal (e.g., sterically large bases and/or less nucleophilic bases). In some cases, bases which are sterically larger than trimethylamine are preferred, provided that the base is not so large as to hinder its participation in the reaction. In some cases, the base may also serve to reduce the occurrence of side reactions such as dimerization (hydrovinylation) and/or isomerization of the starting olefin, for example, by reducing the concentration of M-H, such as Ni—H.

In general, a variety of bases may be used in practice of the present invention. The base may optionally be sterically hindered to discourage metal coordination of the base in those circumstances where such coordination is possible, i.e., alkali metal alkoxides. Examples of bases include, but are not limited to, alkoxides such as sodium t-butoxide, an alkali metal amide such as sodium amide, lithium diisopropylamide or an alkali metal bis(trialkylsilyl)amides such as lithium bis(trimethylsilyl)amide or sodium bis(trimethylsilyl)amide, a tertiary amine (e.g. triethylamine, trimethylamine, Et(i-Pr)$_2$N, Cy$_2$MeN, 4-(dimethylamino)pyridine (DMAP), 2,6-lutadine, N-methylpyrrolidine (NMP), quinuclidine, and the like), 1,5-diazabicycl[4.3.0]non-5-ene (DBN), 1,5-diazabicyclo[5.4.0]undec-5-ene (DBU), alkali and alkaline earth carbonates, alkali and alkaline earth bicarbonates, alkali and alkaline earth hydroxides, alkali and alkaline earth hydrides, (e.g. NaH, LiH, KH, K$_2$CO$_3$, Na$_2$CO$_3$, Tl$_2$CO$_3$, Cs$_2$CO$_3$, K(Ot-Bu), Li(Ot-Bu), Na(Ot-Bu) K(OPh), Na(OPh)), and the like.

Other suitable organic nitrogen bases include quinoline, optionally substituted with allyl or aryl groups, isoquinoline, optionally substituted with alkyl or aryl groups, imidazole, optionally substituted with alkyl or aryl groups, thiazole, optionally substituted with alkyl or aryl groups, and oxazole, optionally substituted with alkyl or aryl groups. In the above compounds, preferred alkyl substitutents may be $C_{1-5}$ alkyl groups and preferred aryl substituents may be $C_{6-20}$ aryl groups, such as phenyl, substituted phenyl, naphthyl, phenanthryl, and the like.

In certain embodiments, Et$_3$N is preferred.

In some embodiments, the base is present in less than or equal to about 2000 mol % relative to the aldehyde. In some embodiments, the base is present in less than or equal to about 1000 mol % relative to the aldehyde. In some embodiments, the base is present in less than or equal to about 600 mol % relative to the aldehyde.

Suitable silicon compounds or silicon-containing compounds which may be used in methods of the invention may include those which are capable of forming a covalent bond with an oxygen atom. In some embodiments, the silicon compound has the formula R$^3$SiX, wherein R$^3$ can be optionally substituted alkyl, optionally substituted cycloalkyl, optionally substituted aryl, optionally substituted heteroaryl, and X can be halide, triflate, or the like. In some embodiments, the silicon compound is trimethylsilyl triflate, triethylsilyl triflate, or tri-t-butylsilyl triflate. In some embodiments, triethylsilyltriflate is the p tert-butyldimethylsilyltriflate referred silyl triflate.

In some embodiments, the silicon compound is present in less than or equal to about 300 mol % relative to the aldehyde. In some embodiments, the silicon compound is present in less than or equal to about 200 mol % relative to the aldehyde. In some embodiments, the silicon compound is present in less than or equal to about 175 mol % relative to the aldehyde.

Solvents which may be used in methods of the invention include inert solvents such as benzene, p-cresol, toluene, xylene, diethyl ether, glycol monomethyl or dimethyl ether, petroleum ether, hexane, cyclohexane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like. Preferred solvents may include benzene, toluene, xylene, ether, hexane, petroleum ether, methylene chloride, chloroform, or tetrahydrofuran. In a particular embodiment, toluene is the preferred solvent.

The products which may be produced by methods of the present invention may undergo further reaction(s) to afford desired derivatives thereof. Such permissible derivatization reactions can be carried out in accordance with conventional procedures known in the art. For example, potential derivatization reactions include cleavage of the oxygen-silicon bond of a silyl ether of an allylic alcohol to afford the allylic alcohol. Suitable reagents which can cleave an oxygen-silicon bond to deprotect an alcohol are known, such as tetrabutylammonium fluoride (TBAF), for example.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, materials, reaction conditions, and configurations described herein are meant to be exemplary and that actual parameters, materials, reaction conditions, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention.

In the claims (as well as in the specification above), all transitional phrases or phrases of inclusion, such as "comprising," "including," "carrying," "having," "containing," "composed of;" "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood, unless otherwise indicated, to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

All references cited herein, including patents and published applications, are incorporated herein by reference. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

EXAMPLES

General Information

Unless otherwise noted, all reactions were performed under an oxygen-free atmosphere of nitrogen or argon with rigid exclusion of moisture from reagents and glassware. Tetrahydrofuran was distilled from a blue solution of sodium benzophenone ketyl. Dichloromethane and toluene was distilled from calcium hydride. All aldehydes were distilled and saturated with nitrogen before use. Bis(cyclooctadienyl)nickel(0) (Ni(cod)$_2$) and tris-(o-methoxyphenyl)-phosphine was purchased from Strem Chemicals, Inc., stored under nitrogen atomosphere and used without further purification. Ethylene was purchased from BOC Gases and used as received. 1-octene, 4-methyl-1-pentene, 7-methyl-1,6-octadiene were purchased from Aldrich Chemical Co. and used as received. Dicyclohexylphenylphosphine was purchased from Aldrich Chemical Co., stored under nitrogen atmosphere and used without further purification. Triethylsilyltrifluoro-methanesulfonate (TESOTf) and trimethylsilyl-trifluoromethansulfonate (TMSOTf) were purchased from Aldrich Chemical Co. and were distilled over calcium hydride before use. Tert-butyldimethysilyl-trifluoromethanesulfonate (TBSOTf) was purchased from Alfa Aesar and was distilled over calcium hydride before use.

Analytical thin layer chromatography (TLC) was performed using EM Science silica gel 60 F$_{254}$ plates. The developed chromatogram was analyzed by UV lamp (254 nm), ethanolic phosphomolybdic acid (PMA) or potassium permanganate (KMnO$_4$). Liquid chromatography was performed using a forced flow (flash chromatography) of the indicated solvent system on Silicycle Silica Gel (230-400 mesh). $^1$H and $^{13}$C NMR spectra were recorded on Varian 300 MHz, Varian 500 MHz or Bruker 400 MHz spectrometers in CDCl$_3$ or C$_6$D$_6$, unless otherwise noted. Chemical shifts in $^1$H NMR spectra are reported in parts per million (ppm) on the δ scale from an internal standard of residual chloroform (7.27 ppm) or residual benzene (7.16 ppm). Data are reported as follows: chemical shift, multiplicity (s=singlet, d=doublet, t=triplet, q=quartet, m=multiplet, b=broad), coupling constant in hertz (Hz), and integration. Chemical shifts of $^{13}$C NMR spectra are reported in ppm from the central peak of CDCl$_3$ (77.23 ppm) on the δ scale. Infrared (IR) spectra were recorded on a Perkin-Elmer 2000 FT-IR. High resolution mass spectra (HRMS) were obtained on a Bruker Daltonics APEX II 3 Tesla Fourier Transform Mass Spectrometer by Dr. Li Li of the Massachusetts Institute of Technology Department of Chemistry Instrument Facility. Chiral GC analysis was performed on a Varian CP-3800 gas chromatograph fitted with Chiraldex B-PH, B-DA, and G-TA capillary columns. Chiral HPLC analysis was performed on a Hewlett-Packard 1100 chromatograph equipped with a variable wavelength detector and Chiralcel OD or OD-H columns. Specific Rotations ([α]$_D$) were measured on a Perkin-Elmer 241 polarimeter at 589 nm.

Example 1

Several reaction conditions were varied in order to more fully investigate the nickel-catalyzed reaction between alpha-olefins and aldehydes to form silyl ethers of allylic alcohol. Investigation into the factors which influence the general mechanistic framework of the reaction may allow one to select optimal reaction conditions to produce a desired product, such as an allylic alcohol or precursor thereof. The effect of the various components (e.g., phosphine, alkene, and aldehyde) which may ligate the metal center during the reaction was studied, as well as the effect of other reaction components, such as the base and nickel source. The interactions of nickel with the phosphine, alkene, and aldehyde may govern the assembly of the oxanickellacycle, which, in turn, may determine the product distribution.

Example 1a

Effect of Phosphine Ligand

One factor that may control the product ratio in the alkene-aldehyde coupling reactions includes the cone angle and/or electronic characteristics (e.g, electron-rich, electron-poor) of the phosphine ligand. In general, the use of large, electron-rich phosphines may favor the allylic alcohol product. For example, dicyclohexylphenylphosphine is electron-rich, has a large cone angle, and is observed to promote formation of the allylic coupling product as the major product. Cone angle and $v_{CO}$ values were obtained from Rahman, M.; Liu, H.-Y.; Eriks, K.; Prock, A.; Giering, W. P. *Organometallics* 1989, 8, 1-7; Tolman, C. A. *Chem. Rev.* 1977, 77, 313-348; Otto, S. *J. Chem. Crystallogr.* 2001, 31, 185190; Riihmaëki, H.; Kangas, T.; Suomalainen, P.; Reinius, H. K.; Jääskeläinen, S.; Haukka, M.; Krause, A. O. I.; Pakkanen, T. A.; Pursiainen, J. T. *J. Mol. Catal. A: Chem.* 2003, 200, 81-94; and, Steinmetz, W. E. *Quant. Struct.-Act. Relat.* 1996, 15, 1-6. To further illustrate the effect of the phosphine ligand on the coupling reaction, various phosphine ligands were employed under similar reaction conditions in the coupling of 1-octene and benzaldehyde, as shown in FIGS. 4 and 5. Different classes of phosphine ligands were observed to favor one or the other coupling products (e.g., 1,2-disubstituted allylic alcohol product (A) or a homoallylic alcohol product (H)). In some cases, the use of $Cy_2PhP$ as the phosphine ligand may favor allylic, rather than homoallylic, alcohol derivatives.

FIG. 4 shows various electron-rich phosphines that were studied. The ratio of the allylic to the homoallylic products was opposite for trialkylphosphines in which all alkyl groups are linear (entries 1 and 2, FIG. 4), relative to those in which the three alkyl groups are branched (entries 3-5, FIG. 4) or tertiary (entry 6, FIG. 4). Among six trialkylphosphines with very similar electron-donating abilities, tri-n-butylphosphine, the smallest of the trialkylphosphines examined, was observed to favore the homoallylic alcohol product, while tricyclohexylphosphine and tri-tert-butylphosphine, the largest among these, was observed to favor the 1,2-disubstituted allylic product. Notably, replacing one of the alkyl substituents of the tricyclohexylphosphine with a phenyl ring dramatically improved the yield (53% vs 16%; FIG. 4, entries 5 and 7) with a slightly increased homoallylic:allylic (H:A) ratio. Other aryldicyclohexylphosphines also displayed a similar yield enhancement (entries 8 and 9, as compared to entries 4-6, FIG. 4). The bulky and electron-rich dicyclohexylferrocenyl-phosphine, however, seemed to be more closely related to tri-tert-butylphosphine (e.g., poor yield for both the allylic and homoallylic alcohol products, entry 10, FIG. 4). All of the sterically demanding dicyclohexylaryl derivatives examined favored the allylic alcohol product. In some cases, dicyclohexylphenylphosphine was the preferred ligand in terms of yield and selectivity.

FIG. 5 shows various electron-poor phosphines that were studied. Among the four tri-arylphosphine ligands with a similar cone angle but different para-substituents (entries 5-7 and 8, FIG. 5), tris-(p-trifluoromethylphenyl)-phosphine, the least electron-rich ligand of the four, produced the highest H:A ratio (entry 8, FIG. 5), whereas tri-p-tolylphosphine, the most sigma-electron-donating among these four ligands, produced the lowest H:A ratio (entry 5, FIG. 4). These data suggest that the ratio of H:A can be modulated at least in part by selecting phosphine ligands having particular sigma-electron-donating properties. That is, a lower H:A ratio can be achieved by increasing the electron-donating ability of the phosphine ligand, while a higher H:A ratio can be achieved by decreasing the electron-donating ability of the phosphine ligand. For example, the following phosphine ligands are listed in increasing sigma-electron-donating ability and, thus, may be predicted to produce increasing amounts of allylic product relative to homoallylic product: $[p-F(C_6H)]_3P$, $[p-Me(C_6H_4)]_3P$, $[o-OMe(C_6H_4)]_3P$, $CyPh_2P$, and $Cy_2PhP$. The sigma-electron-donating ability of a phosphine ligand may be measured by, for example, measuring the relative stretching frequencies of the terminal CO group of $CpFe(CO)LCOMe$ complexes, wherein L is a phosphine ligand, in cyclohexane at room temperature. The CO stretching frequency is a measure of the sigma electron-donating ability to a metal center, where a less electron-donating ligand usually has a higher frequency (see Rahman, M.; Liu, H.-Y.; Eriks, K.; Prock, A.; Giering, W. P. *Organometallics* 1989, 8, 1-7).

Based on the observations, the coupling product (H:A) ratio may be determined by a combined effect of the electron-donating ability and the cone angle of the phosphine ligands. High H:A ratios can be achieved by using less electron-rich phosphines with a small cone angle, while high A:H ratios can be obtained by using electron-rich phosphines with a large cone angle, such as dicyclohexylphenylphosphine ($Cy_2PhP$).

Example 1b

Effect of the Base

Various bases employed under similar reaction conditions in the coupling of ethylene and benzaldehyde, as shown in FIG. 6. In some embodiments, tertiary amines were shown to be preferred bases for the nickel-catalyzed coupling of alkenes and aldehydes. Among different types of amine bases examined in ethylene couplings, only tertiary amines were shown to provide >20% yield of coupling products (entries 1 and 3, FIG. 6). Amines that likely are able to interact with nickel to a greater degree, such as pyridine (entry 5, FIG. 6 and entry 6, FIG. 8) were not observed to be effective. No coupling products were detected when inorganic bases were used in place of triethylamine (entries 6-8, FIG. 6).

Tertiary amines were further examined in the coupling reaction of 1-octene and benzaldehyde (FIG. 7), and triethylamine was consistently superior to other tertiary amines (entries 1-4, FIG. 7). Tertiary amines smaller or larger than triethylamine compromised the yield of the coupling reaction (entries 2-4, FIG. 7). Also, it was observed that a balance of the nucleophilicity, basicity, and steric bulk of the amine base was required for the coupling reaction to occur efficiently. Amines can compete with the phosphorus ligand, alkene, and aldehyde for a coordination site on nickel. A more nucleophilic (sigma-electron-donating) or smaller amine may hinder the coordination of any of the other required components to the nickel catalyst.

In some cases, triethylamine is the preferred base for the nickel-catalyzed coupling of alkenes and aldehydes, potentially due to a combination of low coordinating ability and appropriate basicity.

Example 1c

Effect of the Source of Nickel

Figure 8:
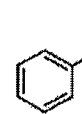
FIG. 8 lists examples of nickel-catalyzed coupling of 1-octene and benzaldehyde using various nickel sources.

Various nickel compounds were employed under similar reaction conditions in the coupling of 1-octene and benzaldehyde, as shown in FIG. 8. Since the precatalyst Ni(cod)$_2$ has two chelating diene ligands (1,5-cyclo-octadiene), other nickel(II) precatalysts without alkene ligands were examined. Ni(cod)$_2$/Cy$_2$PhP was shown to be more efficient than Ni(acac)$_2$Cy2PhP/DIBAL-H and Ni(Cy$_2$PhP)$_2$Cl2/n-BuLi (FIG. 8).

Example 1d

Substrate Scope

The substrate scope of the nickel-catalyzed coupling of alkenes, aldehydes, and silyl triflates was examined, applying the results of the studies of ligand, base, and nickel source effects. FIGS. 9-11 show various coupling reactions using Ni(cod)$_2$, Cy$_2$PhP, and triethylamine as components of the catalyst system. In general, ethylene and monosubstituted alkenes were observed to be reactive substrates in the coupling reaction, while 1,1-disubstituted alkenes, acyclic 1,2-disubstituted (cis or trans) alkenes, and trisubstituted alkenes were observed to be less reactive.

As shown in FIG. 9, propene couples with naphthaldehyde to provide the allylic alcohol product in good yield and with the high selectivity (entry 1, FIG. 9). Aromatic aldehydes and heteroaromatic aldehydes may be coupled with straight chain monosubstituted alkenes in good yield (entries 1-2, 4, FIG. 9). Electron-donating p-anisaldehyde was observed to be more reactive than benzaldehyde (entries 1 and 3, FIG. 9). Therefore, in some cases, a general trend in reactivity may be that electron-donating aldehydes are more reactive than electron-poor aldehydes. Additionally, while branching at the homoallylic position of the alkene may not affect the coupling efficiency (entry 5, FIG. 9), branching at the allylic position may affect the yield of the allylic alcohol product (entry 7, FIG. 9). For example, vinylcy-clohexane produced a lower A:H ratio (entry 7, FIG. 9), with the homoallylic alcohol and a 1,3-disubstituted allylic alcohol formed as the major products.

In order to study competition between substituted alkenes within the same molecule, benzaldehyde was coupled with 7-methyl-1,7-octadiene, which contains both a monosubstituted alkene and a trisubstituted alkene (entry 6, FIG. 9). Benzaldehyde was shown to undergo coupling with the monosubstituted alkene selectively in the presence of the trisubstituted alkene, indicating that the trisubstituted double bond is stable to the reaction conditions. Neither carbocyclization nor isomerization of the trisubstituted double bond in the coupling product was observed. This may enable the use of a trisubstituted double bond as a masked version of other functional groups.

The effect of heteroatoms on the alkene was also investigated (FIGS. 10-11). N-Allylphthalimide, N-homo-allylphthalimide, and N-homoallyloxazolidinone were successfully coupled with aldehydes using the Ni-Cy$_2$PhP system (entries 1-3, FIG. 10). In contrast, allylbenzoate and homoallylbenzoate esters were shown to be much less efficient (entries 1-3, FIG. 11). A small amount of the allylic product was detected only with homoallylbenzoate (entry 2, FIG. 11). When the benzoate group is positioned further away from the terminal double bond, a better yield of the desired coupling product was observed (entry 3, FIG. 11), which may suggest an interaction of the heteroatoms on the alkenes to the nickel catalyst. Without wishing to be bound by theory, the observed difference in reactivity may be that the oxygen on the phthalimide is less nucleophilic and therefore does not bind to the nickel as tightly as the benzoate oxygen. Therefore, the coupling of N-allylphthalimide may occur more efficiently than allylbenzoate (entry 1, FIG. 10 and entry 1, FIG. 11). When the benzoate is positioned further away from the double bond, the benzoate may be less likely to coordinate to the nickel catalyst, and the reactivity of the alkene may be restored (entry 3, FIG. 11).

Example 1d

Effect of Substitution on the Alkene and/or Aldehyde Coupling Partner

The substituents on the alkene and aldehyde coupling partners can also affect the H:A ratio. The alkene substituents can be closer to either the ligand or the aldehyde substituent in the oxanickellacycle. In some cases, allylic alcohol product A (FIG. 13) may be obtained in a significant amount when the alkene has no branching at the allylic position. However, in some cases, branching at the allylic position of the alkene may be tolerated in the coupling process when a relatively small phosphine ligand is used. For example, 3,3-dimethyl-1-butene, a sterically demanding mono-substituted alkene with no allylic hydrogen, provided 1,3-disubstituted allylic alcohol as the sole product.

A large substituent on the aldehyde may favor the production of the homoallylic alcohol. Less than 5% allylic alcohol product was observed when propene or 1-octene was coupled with pivaldehyde with Cy$_2$PhP as the ligand. Without wishing to be bound by theory, the proposed mechanism shown in Scheme 2 shows that, when the beta-hydrogen of oxanickellacycle 1 is not aligned with the C—Ni bond, the —OSiEt$_3$ group can dissociate from nickel to allow bond rotation such that the beta-hydrogen can align with the C—Ni bond, i.e., since beta-hydride elimination generally occurs in the syn orientation. Upon proper alignment between the C—Ni bond and the beta-hydrogen, beta-hydride elimination can occur and allylic product A is formed. The larger the phosphine ligand relative to the aldehyde substituent, the more likely oxanickellacycle 1 may dominate because the alkene substituent may thus avoid severe steric repulsion with this ligand. The data shown in FIG. 4 may support this proposal, as the A:H ratio increases with the cone angle of the trialkylphosphine.

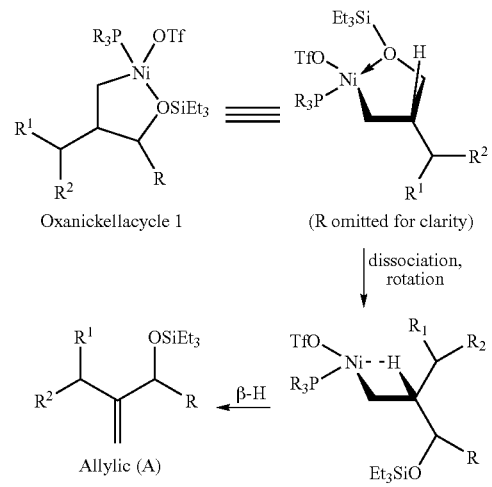

Scheme 2

As shown in Scheme 3, oxanickellacycle 2 may account for the formation of homoallylic alcohol H and allylic alcohol A'. Examination of oxanickellacycle 2 revealed that although the beta-hydrogen in the oxanickellacycle ($H_{endo}$) is not aligned with the C—Ni bond, there are beta-hydrogens outside the oxanickellacycle ($H_{endo}$) that are appropriately poised for beta-hydride elimination once a free coordination site is available. The preferred conformation may align $R^2$ of the alkene trans to the C—C bond of the oxanickellacycle 2. Dissociation of one of the ligands on nickel may provide a free coordination site for the syn beta-hydride elimination to occur and provides the E-homoallylic alcohol H.

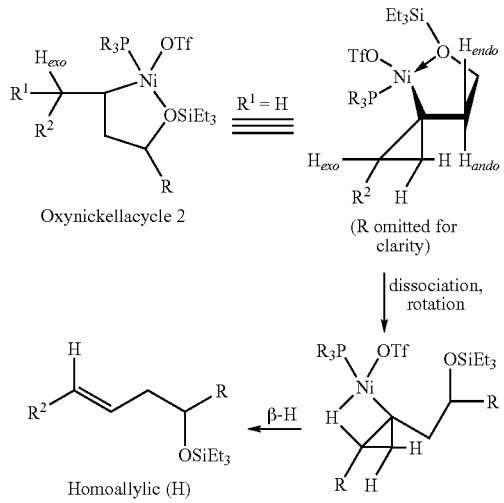

In order for the allylic alcohol (A') to form as shown in FIG. 13, the beta-hydrogens in the oxanickellacycle ($H_{endo}$) may be eliminated instead of the exo-beta-hydrogen ($H_{exo}$). Such a process requires dissociation of —OSiEt$_3$ and may be favored when the exo-beta-hydrogen is not aligned with the C—Ni bond or when there is no exo-beta-hydrogen (Scheme 4). Scheme 4 shows the two mechanistic pathways that may lead to either the homoallylic alcohol product (path a) or the allylic alcohol product (path b). In order for the allylic alcohol to form, endo-beta-hydrogens in the oxanickellacycle ($H_{endo}$) should be eliminated rather than the exo-beta-hydrogen ($H_{exo}$). Such a process would require the dissociation of —SiOEt$_3$ and may be favored when the exo-beta-hydrogen is not aligned with the C—Ni bond or when there is no exo-beta-hydrogen.

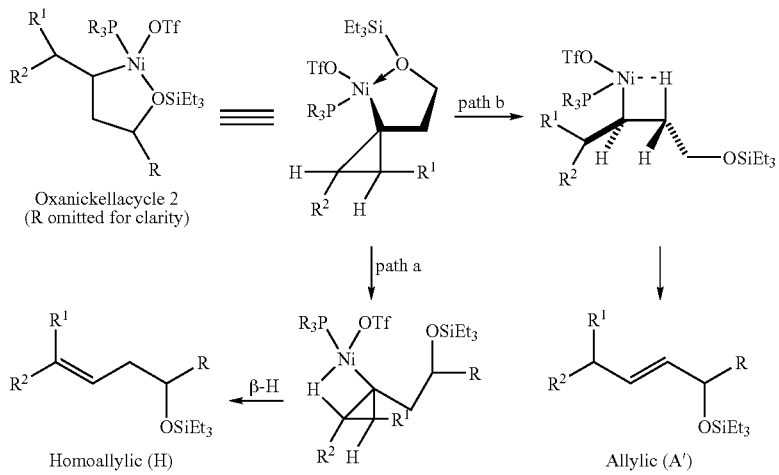

As an illustrative embodiment, the coupling of vinylcyclohexane and benzaldehyde resulted in the formation of 1,3-disubstituted allylic alcohol A'. Neither $R^1$ nor $R^2$ of vinylcyclohexane is a hydrogen atom, and hence the allylic position is very sterically encumbered. Allylic alcohol product A may not be favored because the large substituent of vinylcyclohexane may not be accommodated next to the aldehyde substituent (R) in oxanickellacycle 1 (Scheme 2) due to severe steric repulsion.

Experimental data supporting this theory includes the fact that the coupling of vinylcyclohexane with benzaldehyde using Cy$_2$PhP as ligand yields only 5% of the allylic alcohol product A (FIG. 9, entry 7), as compared with other unbranched alkenes in FIG. 9, entries 1-6). Using a smaller ligand, the large substituents in vinylcyclohexane can be accommodated by being closer to the ligand than to the aldehyde substituent, favoring oxanickellacycle 2 (Scheme 3). The exo-beta-hydrogen of the oxanickellacycle, when aligned with the C—Ni bond, can induce an unfavorable steric interaction between the cyclohexyl group and the C—C bond of the oxanickellacycle. Therefore the rate of beta-hydride elimination from the exo-beta-hydrogen may decrease, and that of the endo-beta-hydrogen may increases, resulting in a greater amount of the E-allylic product A'. The E-double-bond geometry of A' may be obtained by minimizing steric repulsion during the beta-H elimination step.

In some cases, alkenes without an allylic hydrogen cannot afford homoallylic alcohol products in the nickel-catalyzed alkene-aldehyde coupling reaction. For example, 3,3-dimethyl-1-butene, with no allylic hydrogen, couples with benzaldehyde to give exclusively E-1,3-disubstituted allylic alcohol product (A'). Also, the steric bulk of the tert-butyl group may render formation of oxanickellacycle 1 extremely difficult, reducing the possibility of affording 1,2-disubstituted allylic alcohol product A.

Evidence for the beta-hydride elimination as the next step may be the observation of isomerization and dimerization (hydrovinylation) of the starting olefins, which may suggest the presence of a nickel-hydride (Ni—H) species, likely formed by a beta-hydride elimination. The requirement of a base in some catalyst systems also supports the presence of a Ni—H species. As shown in FIG. 12, beta-hydride elimination and subsequent base-assisted removal of triflic acid (reductive elimination) from the Ni—H species can regenerate the Ni(0) catalyst and may also minimize side reactions by suppressing the presence of the Ni—H species.

Example 2

Preparation of 2,2-Dimethyl-3-oxo-propionic Acid Methyl Ester

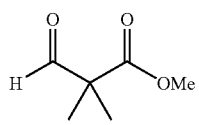

3-Hydroxy-2,2-dimethyl-propionic acid methyl ester (15 g, 113 mmol) in 200 mL dichloromethane was cooled to 0° C. Pyridinium chlorochromate (43 g, 200 mmol) was added. The mixture was slowly warmed to room temperature and stirred 24 h. The crude in dichloromethane was filtered through silica gel. Celite was added to the remaining black viscous oil from the reaction mixture until the viscous oil is all absorbed to the celite. Dichloromethane was added to this slurry and the dichloromethane solution was filtered through silica gel. Dichloromethane was removed at reduced pressure (80 Torr) to give a pale yellow crude. Distillation removed residue dichloromethane and obtained 2,2-dimethyl-3-oxo-propionic acid methyl ester as a colorless oil (7 g, 48% yield). $^1$H NMR (300 MHz, CDCl$_3$, δ): 9.60 (s, 1H); 3.70 (s, 3H); 1.29 (s, 6H). $^{13}$C NMR (75 MHz, CDCl$_3$, δ): 199.1, 173.2, 53.9, 52.6, 19.7. IR (NaCl, thin film): 2988, 2958, 1726, 1468, 1278, 1151, 866.

Example 3

Nickel-Catalyzed Couplings of Ethylene and Liquid Aldehydes

General procedure 1: A 10 mL round bottom flask and a stir bar were oven-dried and brought into a glove box. Ni(cod)$_2$ (27.5 mg, 0.1 mmol, 20 mol %) and tris-o-methoxyphenylphosphine (70.5 mg, 0.2 mmol, 40 mol %) were added to the round bottom flask, the flask was sealed with a septum, and the sealed flask was brought out of the glove box and connected to an argon line. The catalyst mixture was dissolved in toluene (2.5 mL) under argon and stirred 15 min at room temperature. The reaction mixture was purged with ethylene for 1 min to remove argon, taking care not to introduce oxygen. The ethylene atmosphere was maintained with an ethylene balloon. Next triethylamine (418 µL, 3 mmol, 600 mol %) was added. Silyltriflate (0.875 mmol, 175 mol %, as specified) was added. Aldehyde (0.5 mmol, 100 mol %, as specified) was added. The mixture was stirred at room temperature for 3-18 h. The mixture was filtered through a plug of silica gel. Solvent was removed under reduced pressure and the crude mixture was diluted in hexane. Purification via flash chromatography on silica afforded the coupling product.

General procedure 2: A 10 mL round bottom flask and a stir bar were oven-dried and brought into a glove box. Ni(cod)$_2$ (27.5 mg, 0.1 mmol, 20 mol %), tris-o-methoxyphenyl-phosphine (70.5 mg, 0.2 mmol, 40 mol %) and aldehyde (0.5 mmol, 100 mol %) were added to the round bottom flask, the flask was sealed with a septum, and the sealed flask was brought out of the glove box and connected to an argon line. The catalyst mixture was dissolved in toluene (2.5 mL) under argon and stirred 15 min at room temperature. The reaction mixture was purged with ethylene for 1 min to remove argon, taken care not to introduce oxygen. The ethylene atmosphere was maintained with an ethylene balloon. Next triethylamine (418 µL, 3 mmol, 600 mol %) was added. Silyltriflate (0.875 mmol, 175 mol %, as specified) was added. The mixture was stirred at room temperature for 3-18 h, as judged by TLC of the reaction mixture. The mixture was filtered through a plug of silica gel. Solvent was removed under reduced pressure and the crude mixture was diluted in hexane. Purification via flash chromatography on silica afforded the coupling product.

Example 4

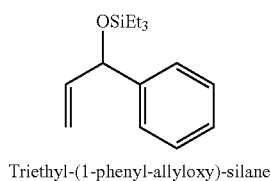

Triethyl-(1-phenyl-allyloxy)-silane

The reaction of ethylene and benzaldehyde (51 µL, 0.5 mmol) with Ni(cod)$_2$, tris-o-methoxyphenylphosphine and TESOTf (197 µL, 0.875 mmol), triethylamine in toluene following general procedure 1 above, afforded the title compound in 82% isolated yield as a colorless oil. $^1$H NMR (400 MHz, CDCl$_3$, δ): 7.32-7.45 (m, 4H); 7.29 (t, J=7.0 Hz, 1H); 6.01 (ddd, J=6.0, 10.2, 16.9 Hz, 1H); 5.34 (dt, J=1.5, 16.9 Hz, 1H); 5.25 (d, J=5.9 Hz, 1H); 5.13 (dt, J=1.5, 10.2 Hz, 1H); 0.99 (t, J=8.0 Hz, 9H); 0.66 (dq, J=1.8, 7.8 Hz, 6H).
$^{13}$C NMR (100 MHz, CDCl$_3$, δ): 143.9, 141.8, 128.4, 127.3, 126.2, 113.7, 75.9, 7.0, 5.1. IR (NaCl, thin film): 2956, 2877, 1640, 1454, 1240, 1065, 744, 699. HRMS-ESI (m/z): [M+Na]$^+$ calcd for C$_{15}$H$_{24}$OSi, 271.149; found, 271.150.

Example 5

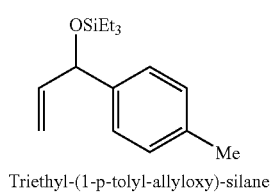

Triethyl-(1-p-tolyl-allyloxy)-silane

The reaction of ethylene and p-tolualdehyde (59 µL, 0.5 mmol) with Ni(cod)$_2$, tris-o-methoxyphenylphosphine and TESOTf (197 µL, 0.875 mmol), triethylamine in toluene following general procedure 1 above, afforded the title compound in 88% isolated yield as a colorless oil. $^1$H NMR (400 MHz, CDCl$_3$, δ): 7.27 (d, J=8.0, 2H); 7.16 (d, J=8.0 Hz, 2H); 5.97 (ddd, J=5.9, 10.2, 16.9 Hz, 1H); 5.30 (dt, J=1.5, 17.0 Hz, 1H); 5.17 (d, J=5.9 Hz, 1H); 5.09 (dt, J=1.3, 10.2 Hz, 1H); 2.37 (s, 3H); 0.97 (t, J=7.9 Hz, 9H); 0.65 (dq, J=1.9, 7.5 Hz, 6H). $^{13}$C NMR (100 MHz, CDCl$_3$, δ): 142.1, 141.1, 136.8, 129.1, 126.2, 113.4, 75.8, 21.3, 7.0, 5.2. IR (NaCl, thin film):

Example 6

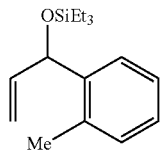

Triethyl-(1-o-tolyl-allyloxy)-silane

The reaction of ethylene and o-tolualdehyde (58 µL, 0.5 mmol) with Ni(cod)$_2$, tris-o-methoxyphenylphosphine and TESOTf (197 µL, 0.875 mmol), triethylamine in toluene following general procedure 1 above, afforded the title compound in 93% isolated yield as a colorless oil. $^1$H NMR (400 MHz, CDCl$_3$, δ): 7.50 (d, J=7.0, 1H); 7.11-7.24 (m, 4H); 5.93 (ddd, J=5.7, 10.2, 17.0 Hz, 1H); 5.36 (d, J=5.6 Hz, 1H); 5.22 (dt, J=1.6, 17.1 Hz, 1H); 5.08 (dt, J=1.5, 10.2 Hz, 1H); 2.34 (s, 3H); 0.95 (t, J=8.0 Hz, 9H); 0.61 (dq, J=2.8, 7.5 Hz, 6H). $^{13}$C NMR (100 MHz, CDCl$_3$, δ): 141.9, 140.7, 134.4, 130.3, 127.1, 126.5, 126.3, 113.7, 73.1, 19.4, 7.0, 5.1. IR (NaCl, thin film): 2955, 2877, 1639, 1461, 1066, 1007, 744. HRMS-ESI (m/z): [M+Na]$^+$ calcd for C$_{16}$H$_{26}$OSi, 285.165; found, 285.165.

Example 7

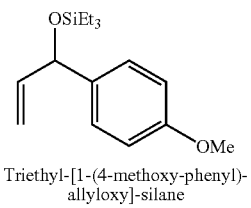

Triethyl-[1-(4-methoxy-phenyl)-allyloxy]-silane

The reaction of ethylene and p-anisaldehyde (61 µL, 0.5 mmol), with Ni(cod)$_2$, tris-o-methoxy-phenylphosphine and TESOTf (197 µL, 0.875 mmol), triethylamine in toluene following general procedure 1 above, afforded the title compound in 95% isolated yield as a colorless oil. $^1$H NMR (400 MHz, CDCl$_3$, δ): 7.30 (d, J=8.7 Hz, 2H); 6.90 (d, J=8.7 Hz, 2H); 5.97 (ddd, J=5.9, 10.2, 16.9 Hz, 1H); 5.29 (dt, J=1.4, 17.0 Hz, 1H); 5.16 (d, J=5.9 Hz, 1H); 5.10 (dt, J=1.4, 10.2 Hz, 1H); 3.83 (s, 3H); 0.96 (t, J=7.9 Hz, 9H); 0.63 (dq, J=1.8, 7.5 Hz, 6H). $^{13}$C NMR (100 MHz, CDCl$_3$, δ): 158.9, 142.0, 136.2, 127.4, 113.7, 113.4, 75.4, 55.4, 7.0, 5.1. IR (NaCl, thin film): 2955, 2877, 1639, 1511, 1464, 1246, 1037, 744. HRMS-ESI (m/z): [M+Na]$^+$ calcd for C$_{16}$H$_{26}$O$_2$Si, 301.159; found, 301.159.

Example 8

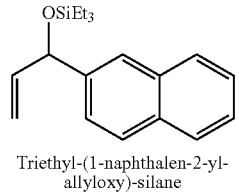

Triethyl-(1-naphthalen-2-yl-allyloxy)-silane

The reaction of ethylene and 2-naphthaldehyde with Ni(cod)$_2$, tris-o-methoxyphenylphosphine and TESOTf (197 µL, 0.875 mmol), triethylamine in toluene following general procedure 2 above, afforded the title compound in 95% isolated yield as a colorless oil. $^1$H NMR (400 MHz, CDCl$_3$, δ): 7.82-7.92 (m, 4H); 7.48-7.55 (m, 3H); 6.07 (ddd, J=6.2, 10.2, 15.8 Hz, 1H); 5.35-5.45 (m, 2H); 5.17 (dt, J=1.3, 10.1 Hz, 1H); 1.00 (t, J=7.8 Hz, 9H); 0.68 (dq, J=2.5, 7.5 Hz, 6H). $^{13}$C NMR (100 MHz, CDCl$_3$, δ): 141.7, 141.4, 133.5, 133.0, 128.2, 128.1, 127.7, 126.1, 125.8, 124.8, 124.6, 114.0, 76.0, 7.0, 5.1. IR (NaCl, thin film): 2955, 2876, 1640, 1458, 1239, 1006, 743. HRMS-ESI (m/z): [M+Na]$^+$ calcd for C$_{19}$H$_{26}$OSi, 321.165; found, 321.164.

Example 9

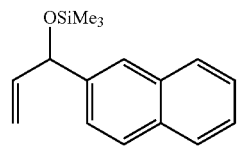

Trimethyl-(1-naphthalen-2-yl-allyloxy)-silane

The reaction of ethylene and 2-naphthaldehyde with Ni(cod)$_2$, tris-o-methoxyphenylphosphine and TMSOTf (158 µL, 0.875 mmol), triethylamine in toluene following general procedure 2 above, afforded the title compound in 60% isolated yield as a colorless oil. $^1$H NMR (400 MHz, CDCl$_3$, δ): 7.80-7.90 (m, 4H); 7.45-7.54 (m, 3H); 6.06 (ddd, J=5.6, 10.2, 17.4 Hz, 1H); 5.30 (dt, J=1.5, 17.3 Hz, 1H); 5.37 (bs, 1H); 5.17 (dt, J=1.4, 10.2 Hz, 1H); 0.18 (s, 9H). $^{13}$C NMR (100 MHz, CDCl$_3$, δ): 141.4, 141.0, 133.5, 133.0, 128.19, 128.18, 127.9, 126.2, 125.9, 124.9, 124.8, 114.4, 76.1, 0.4. IR (NaCl, thin film): 2958, 1640, 1251, 1077, 841. HRMS-ESI (m/z): [M+Na]$^+$ calcd for C$_{16}$H$_{20}$OSi, 279.118; found, 279.119.

Example 10

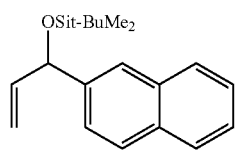

Tert-Butyl-dimethyl-(1-naphthalen-2-yl-allyloxy)-silane

The reaction of ethylene and 2-naphthaldehyde with Ni(cod)$_2$, tris-o-methoxyphenylphosphine and TBSOTf (201 μL, 0.875 mmol), triethylamine in toluene following general procedure 2 above, afforded the title compound in 67% isolated yield as a colorless oil. $^1$H NMR (400 MHz, CDCl$_3$, δ): 7.80-7.92 (m, 4H); 7.45-7.55 (m, 3H); 6.04 (ddd, J=5.8, 10.2, 16.8 Hz, 1H); 5.39 (dt, J=1.5, 17.0, 1H); 5.38 (s, 1H); 5.14 (dt, J=1.5, 10.2 Hz, 1H); 0.99 (s, 9H); 0.16 (s, 3H); 0.06 (s, 3H). $^{13}$C NMR (100 MHz, CDCl$_3$, δ): 141.8, 141.4, 133.5, 133.0, 128.2, 128.1, 127.9, 126.1, 125.8, 124.8, 124.6, 113.8, 76.2, 26.1, 18.6, −4.4, −4.6. IR (NaCl, thin film): 2956, 2857, 1636, 1472, 1252, 1081, 837. HRMS-ESI (m/z): [M+Na]$^+$ calcd for C$_{19}$H$_{26}$OSi, 321.165; found, 321.164.

Example 11

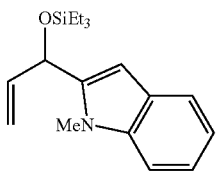
(1h)

The reaction of ethylene and 1-methyl-2-indolecarboxaldehyde (79.6 mg, 0.5 mmol) with Ni(cod)$_2$, tris-o-methoxyphenylphosphine, and TESOTf (197 μL, 0.875 mmol), triethylamine in toluene following the general procedure 2 above, afforded 1 h in 67% isolated yield as a colorless oil. $^1$H NMR (400 MHz, CDCl$_3$, δ): 7.63 (d, J=7.8 Hz, 1H); 7.36 (d, J=8.2 Hz, 1H); 7.26 (t, J=8.3 Hz, 1H); 7.14 (t, J=7.9 Hz, 1H); 6.43 (s, 1H); 6.13 (ddd, J=4.5, 10.3, 17.1 Hz, 1H); 5.52 (ddd, J=1.7, 1.7, 4.5 Hz, 1H); 5.39 (ddd, J=1.7, 1.7, 17.1 Hz, 1H); 5.25 (ddd, J=1.7, 1.7, 10.4 Hz, 1H); 3.82 (s, 3H); 0.98 (t, J=8.0 Hz, 9H); 0.66 (dq, J=1.4, 8.0 Hz, 6H). $^{13}$C NMR (100 MHz, CDCl$_3$, δ): 140.6, 139.7, 138.5, 127.5, 121.5, 120.8, 119.4, 114.9, 109.1, 100.5, 70.4, 31.0, 7.0, 5.0. IR (NaCl, thin film): 2955, 2911, 2876, 1911, 1758, 1641, 1469, 1238, 1009, 841, 731. HRMS-ESI(m/z): [M+Na]$^+$ calcd for C$_{18}$H$_{27}$NOSiNa, 324.178; found, 324.178.

Example 12

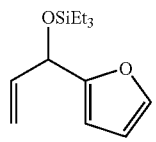
(1i)

The reaction of ethylene and furan-2-carbaldehyde (41 μL, 0.5 mmol) with Ni(cod)$_2$, tris-o-methoxyphenylphosphine, and TESOTf (197 μL, 0.875 mmol), triethylamine in toluene following the general procedure 1 above, afforded 1i in 38% isolated yield as a colorless oil. $^1$H NMR (400 MHz, CDCl$_3$ δ): 7.37 (bs, 1H); 6.32 (dd, J=1.9, 3.1 Hz, 1H); 6.22 (d, J=3.2 Hz, 1H); 6.06 (m, 1H); 5.40 (d, J=17.1 Hz, 1H); 5.21 (d, J=7.9 Hz, 2H); 0.95 (t, J=7.9 Hz, 9H); 0.63 (q, J=7.9 Hz, 6H). $^{13}$C NMR (100 MHz, CDCl$_3$, δ): 156.0, 142.1, 138.1, 115.3, 110.4, 106.4. 69.3, 6.9, 4.9. IR (NaCl, thin film): 2956, 2878, 1646, 1459, 1237, 1010, 733. HRMS-ESI(m/z): [M+Na]$^+$ calcd for C$_{13}$H$_{22}$O$_2$SiNa, 261.128; found, 261.129.

Example 13

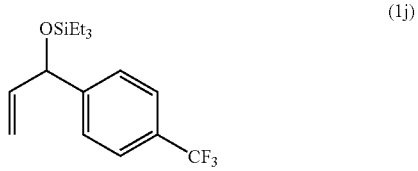
(1j)

The reaction of ethylene and 4-(trifluoromethyl)-benzaldehyde (70 μL, 0.5 mmol) with Ni(cod)$_2$, tris-o-methoxyphenylphosphine and TESOTf (197 μL, 0.875 mmol), triethylamine in toluene following general procedure 1 above, afforded a mixture of 1j and triethylsilylethers of pinnacol coupling products. This mixture was subjected to TBAF to isolate 25% of the desilylated 1j as a colorless oil.

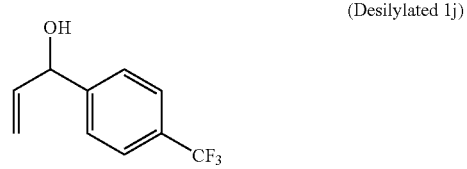
(Desilylated 1j)

$^1$H NMR (400 MHz, CDCl$_3$, δ): 7.62 (d, J=8.2 Hz, 2H); 7.50 (d, J=8.4 Hz, 2H); 6.02 (ddd, J=6.3, 10.3, 16.9 Hz, 1H); 5.38 (ddd, J=1.2, 1.2, 17.0 Hz, 1H); 5.27 (bd, J=7.0 Hz, 1H); 5.25 (ddd, J=1.2, 1.2, 10.3 Hz, 1H); 2.10 (bs, 1H). $^{13}$C NMR (100 MHz, CDCl$_3$, δ): 146.5, 139.8, 130.0 (J=32.3 Hz), 126.7, 125.7, 123.0, 116.4, 75.1. $^{19}$F NMR (376 MHz, CDCl$_3$, δ): −66.8 (s, 3F). IR(NaCl, thin film): 3342, 1620, 1419, 1328, 1166, 1126, 1068, 931. HRMS-ESI (m/z): [M+Na]$^+$ calcd for C$_{10}$H$_9$OF$_3$Na, 202.060; found, 202.059.

Example 14

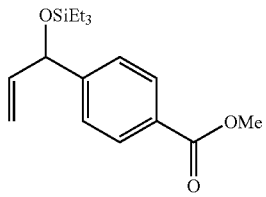
(1k)

The reaction of ethylene and methyl-4-formyl-benzoate (88 mg, 0.536 mmol) with Ni(cod)$_2$, tris tris-o-methoxyphenylphosphine and TESOTf (197 μL, 0.875 mmol), triethylamine in toluene following general procedure 2 above, afforded 1k in 34% isolated yield as a colorless oil. $^1$H NMR (400 MHz, CDCl$_3$, δ): 8.01 (d, J=8.4 Hz, 2H); 7.43 (d, J=8.1 Hz, 2H); 5.92 (ddd, J=6.0, 10.2, 16.9 Hz, 1H); 5.31 (ddd, J=1.5, 1.5, 17.0 Hz, 1H); 5.21 (bd, J=6.0 Hz, 1H); 5.11 (ddd, J=1.4, 1.4, 10.2 Hz, 1H); 3.91 (s, 3H); 0.93 (t, J=7.8 Hz, 9H); 0.61 (dq, J=1.7, 7.5 Hz, 6H). $^{13}$C NMR (100 MHz, CDCl$_3$, δ): 167.2, 149.1, 141.1, 129.8, 129.1, 126.1, 114.5, 75.6, 52.2, 6.9, 5.0. IR (NaCl, thin film): 2954, 2912, 2877, 1727, 1610, 1436, 1278, 1113, 1019, 842, 745. HRMS-ESI (m/z): [M+Na]+ calcd for $C_{17}H_{26}O_3SiNa$, 329.154; found, 329.155.

Example 15

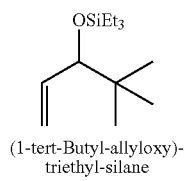

(1-tert-Butyl-allyloxy)-triethyl-silane

The reaction of ethylene and pivaldehyde (55 μL, 0.5 mmol) with Ni(cod)$_2$, tris-o-methoxyphenylphosphine and TESOTf (197 μL, 0.875 mmol), triethylamine in toluene following general procedure 1 above, afforded 11 in 70% isolated yield as a colorless oil. $^1$H NMR (400 MHz, CDCl$_3$, δ): 5.97 (ddd, J=5.9, 10.2, 16.9 Hz, 1H); 5.12 (bs, 1H); 5.10 (bs, 1H); 5.08 (bs, 1H); 3.67 (d, J=7.5 Hz, 1H); 0.96 (t, J=7.9 Hz, 9H); 0.86 (s, 9H); 0.63 (q, J=7.7 Hz, 6H). $^{13}$C NMR (100 MHz, CDCl$_3$, δ): 139.4, 115.8, 82.4, 35.5, 26.0, 7.2, 5.3. IR (NaCl, thin film): 2955, 2877, 1641, 1462, 1239, 1082, 835.

Example 16

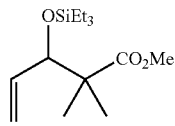

2,2-Dimethyl-3-triethylsilanyloxy-pent-4-enoic acid methyl ester (1m)

The reaction of ethylene and 2,2-dimethyl-3-oxo-propionic acid methyl ester (70 mg, 0.54 mmol) with Ni(cod)$_2$, tris-o-methoxyphenylphosphine and TESOTf (197 μL, 0.875 mmol), triethylamine in toluene following general procedure 1 above, afforded the title compound in 81% (0.28 mmol) isolated yield as a colorless oil. $^1$H NMR (400 MHz, CDCl$_3$, δ): 5.75 (ddd, J=7.6, 10.4, 17.5 Hz, 1H); 5.17 (bd, J=17.3 Hz, 1H); 5.15 (bd, J=10.3 Hz, 1H); 5.10 (dt, J=1.4, 10.2 Hz, 1H); 4.31 (d, J=7.6 Hz, 1H); 3.66 (s, 3H); 1.15 (s, 3H); 1.05 (s, 3H); 0.92 (t, J=7.9 Hz, 9H); 0.55 (dq, J=1.5, 7.6 Hz, 6H). $^{13}$C NMR (100 MHz, CDCl$_3$, δ): 177.4, 137.8, 117.3, 79.2, 51.8, 48.3, 21.4, 19.9, 7.0, 5.2. IR (NaCl, thin film): 2954, 2878, 1745, 1732, 1642, 1468, 1261, 1087, 834. HRMS-ESI (m/z): [M+Na]+ calcd for $C_{14}H_{28}O_3Si$, 295.170; found, 295.171.

Example 17

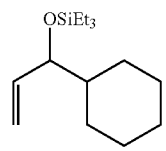

The reaction of ethylene and cyclohexanecarboxaldehyde (60 μL, 0.5 mmol) with Ni(cod)$_2$, tris-o-methoxyphenylphosphine and TESOTf (197 μL, 0.875 mmol), triethylamine in toluene following general procedure 1 above, afforded the title compound in 25% yield as determined by $^1$H NMR versus a standard. Another experiment was carried out under 2 atm of ethylene and yielded 34% of the title compound and 66% silyl enol ether of cyclohexanecarboxaldehyde. Treatment of this mixture with a TBAF/THF/H$_2$O solution removed the silyl enol ether from the mixture and column chromatography isolated 1n as a colorless oil. $^1$H NMR (400 MHz, CDCl$_3$, δ): 5.78 (ddd, J=7.0, 10.3, 17.3 Hz, 1H); 5.07 (m, 2H); 3.78 (t, J=6.6 Hz, 1H); 1.40-0.90 (m, 11H); 0.95 (t, J=8.0 Hz, 9H); 0.59 (q, J=8.0 Hz, 6H). $^{13}$C NMR (125 MHz, CDCl$_3$, δ): 140.7, 114.8, 78.9, 44.5, 29.0, 29.0, 26.9, 26.5, 26.5, 7.1, 5.2. IR (NaCl, thin film): 2953, 2926, 2877, 1644, 1451, 1239, 1068, 743. HRMS-ESI (m/z): [M+Na]+ calcd for $C_{15}H_{30}OSiNa$, 277.196; found, 277.197.

Example 18

Nickel-Catalyzed Coupling of Monosubstituted Alkenes and Aldehydes

General procedure 3: A 10 mL test tube and a stir bar were oven-dried and brought into a glove box. Ni(cod)$_2$ (27.5 mg, 0.1 mmol, 20 mol %) and ligand (0.2 mmol, 40 mol % as specified) were added to the test tube, the test tube was sealed with a septum, and the sealed tube was brought out of the glove box and connected to an argon line. The catalyst mixture was dissolved in toluene (2.5 mL) under argon and stirred 5 min at room temperature. Alkene (0.5 mL), triethylamine (418 μL, 3 mmol, 600 mol %) and then aldehyde (0.5 mmol, 100 mol %) were added. TESOTf (197 μL, 0.875 mmol, 175 mol %) was added. The mixture was stirred at room temperature for 48 h. The mixture was filtered through a plug of silica gel. Solvent was removed under reduced pressure and the crude mixture was diluted in hexane. Purification via flash chromatography on silica afforded the coupling product.

Example 19

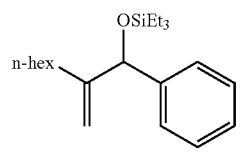

Triethyl-(2-methylene-1-phenyl-octyloxy)-silane (2b')

The reaction of 1-octene (1 mL) and benzaldehyde (51 μL, 0.5 mmol) with Ni(cod)$_2$, Cy$_2$PhP (56 mg, 0.2 mmol, 40 mol %) and TESOTf (197 μL, 0.875 mmol), triethylamine in toluene following general procedure 3 above afforded a mixture of allylic product and homoallylic product in 73% total yield according to $^1$H NMR of the crude mixture and the ratio of allylic:homoallylic product was 71:29. Purification via flash chromatography on silica afforded the product as a colorless oil.

$^1$H NMR (400 MHz, CDCl$_3$, δ): 7.36 (d, J=7.0 Hz, 2H); 7.31 (t, J=7.1 Hz, 2H); 7.24 (t, J=7.2 Hz, 1H); 5.22 (bs, 1H); 5.15 (bs, 1H); 4.87 (s, 1H); 1.96 (pentet, J=7.8 Hz, 1H); 1.76 (pentet, J=8.0 Hz, 1H); 1.15-1.40 (m, 8H); 0.93 (t, J=8.0 Hz, 9H); 0.87 (t, J=6.8 Hz, 3H); 0.60 (dq, J=1.6, 7.9 Hz, 6H). $^{13}$C NMR (100 MHz, CDCl$_3$, δ): 152.3, 143.8, 128.1, 127.1, 126.6, 109.5, 78.3, 32.0, 30.8, 29.4, 28.0, 22.8, 14.3, 7.0, 5.1.

IR (NaCl, thin film): 2956, 2876, 1647, 1456, 1089, 1066, 742. HRMS-ESI (m/z): [M+Na]+ calcd for $C_{21}H_{36}OSi$, 355.243; found, 355.242.

Example 20

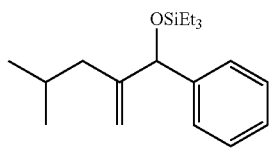

Triethyl-(4-methyl-2-methylene-1-phenyl-pentyloxy)-silane (2n')

A 10 mL round bottom flask and a stir bar were oven-dried and brought into a glove box. Ni(cod)$_2$ (27.5 mg, 0.2 mmol, 20 mol %) and dicyclohexylphenylphosphine (55 mg, 0.4 mmol, 40 mol %) were added to the round bottom flask, the flask was sealed with a septum, and the sealed flask was brought out of the glove box and connected to an argon line. The catalyst mixture was dissolved in toluene (2.5 mL) under argon and stirred 5 min at room temperature. 4-Methyl-1-pentene (633 µL, 5 mmol, 1000 mol %) was added. Triethylamine (418 µL, 3 mmol, 600 mol %) was added. TESOTf (197 µL, 0.875 mmol, 175 mol %) was added. Benzaldehyde (51 µL, 0.5 mmol, 100 mol %) was added to the reaction mixture. The mixture was stirred at room temperature for 14 h. The mixture was filtered through a plug of silica gel. Solvent was removed under reduced pressure and the crude mixture was diluted in hexane. Purification via flash chromatography on silica afforded the title compound in 44% isolated yield as a colorless oil.

The reaction can also be performed according to general procedure 3, which also afforded the product in similar yield.

$^1$H NMR (400 MHz, CDCl$_3$, δ): 7.36 (d, J=7.8 Hz, 2H); 7.32 (t, J=7.1 Hz, 2H); 7.25 (t, J=7.1, 1H); 5.30 (bs, 1H); 5.12 (bs, 1H); 4.87 (bs, 1H); 1.65-1.85 (m, 3H); 0.93 (t, J=308.0 Hz, 9H); 0.84 (d, J=6.4 Hz, 3H); 0.82 (d, J=6.2 Hz, 3H); 0.60 (dq, J=1.3, 8.3 Hz, 6H). $^{13}$C NMR (100 MHz, CDCl$_3$, δ): 150.5, 143.7, 128.1, 127.1, 126.7, 110.7, 77.9, 41.1, 26.3, 23.0, 22.6, 7.0, 5.0. IR (NaCl, thin film): 2955, 2877, 1646, 1454, 1088, 1067, 743. HRMS-ESI (m/z): [M+Na]+ calcd for $C_{19}H_{32}OSi$, 327.211; found, 327.212.

Example 21

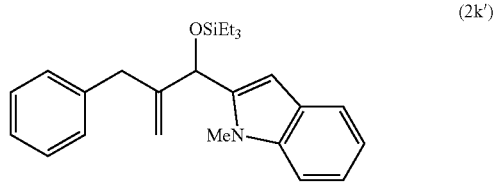

(2k')

The reaction of allylbenzene and 1-methyl-2-indolecarboxaldehyde (79.6 mg, 0.5 mmol) with Ni(cod)$_2$, Cy$_2$PhP (56 mg, 0.2 mmol, 40 mol %) and TESOTf (197 µL, 0.875 mmol), triethylamine in toluene following general procedure 3 above afforded a mixture of allylic product and homoallylic product in 56% total yield according to $^1$H NMR of the crude mixture and the ratio of allylic:homoallylic product was 80:20. The mixture was subjected to TBAF and 2k' was isolated by flash chromatography on silica (buffered with Et$_3$N) as colorless oils. $^1$H NMR (400 MHz, CDCl$_3$, δ): 7.63 (d, 1H); 7.12-7.38 (m, 8H); 6.49 (s, 1H); 5.38 (s, 1H); 5.31 (s, 1H); 5.14 (s, 1H); 3.70 (s, 3H); 3.54 (d, J=15.3 Hz, 1H); 3.33 (d, J=15.3 Hz, 1H); 1.98 (d, J=5.1 Hz, 1H). $^{13}$C NMR (100 MHz, CDCl$_3$, δ): 148.7, 139.6, 139.1, 138.4, 129.3, 128.6, 127.3, 126.6, 122.0, 121.0, 119.7, 113.2, 109.3, 101.5, 69.6, 40.2, 30.3. IR (NaCl, thin film): 3349, 3059, 3027, 2923, 1649, 1601, 1494, 1468, 1453, 1318, 1234, 1030, 968, 907, 751, 737, 700. HRMS-ESI (m/z): [M+Na]+ calcd for $C_{19}H_{19}NONa$, 300.1364; found, 300.1369.

Example 22

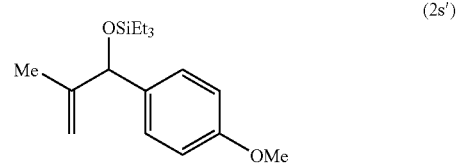

(2s')

A 10 mL round bottom flask and a stir bar were oven-dried and brought into a glove box. Ni(cod)$_2$ (28 mg, 0.1 mmol, 20 mol %), dicyclohexylphenylphosphine (56 mg, 0.2 mmol, 40 mol %) and 2-naphthaldehyde (78 mg, 0.5 mmol, 100 mol %) were added to the round bottom flask, the flask was sealed with a septum, and the sealed flask was brought out of the glove box and connected to an argon line. The catalyst mixture was dissolved in toluene (2.5 mL) under argon and stirred 5 min at room temperature. The system was purged with propene for 1 min. The propene atmosphere was maintained by a propene balloon. Triethylamine (418 µL, 3 mmol, 600 mol %) was added. TESOTf (197 µL, 0.875 mmol, 175 mol %) was added. The mixture was stirred at room temperature for 6 h. The mixture was diluted with hexane and filtered through a plug of silica gel. Solvent was removed under reduced pressure. Purification via flash chromatography on silica afforded 2s' in 73% isolated yield as a colorless oil. $^1$H NMR (400 MHz, CDCl$_3$, δ): 7.86 (m, 4H); 7.50 (m, 3H); 5.33 (s, 1H); 5.26 (s, 1H); 4.94 (s, 1H); 1.62 (s, 3H); 1.00 (t, J=8.0 Hz, 9H); 0.67 (dq, J=1.8, 7.9 Hz, 6H). $^{13}$C NMR (100 MHz, CDCl$_3$, δ): 148.0, 141.0, 133.4, 133.0, 128.2, 127.8, 127.8, 126.0, 125.7, 124.9, 124.8, 78.6, 17.6, 7.1, 5.1. IR (NaCl, thin film): 2955, 2912, 2876, 1652, 1508, 1457, 1238, 1084, 1005, 899, 742. HRMS-ESI (m/z): [M+Na]+ calcd for $C_{20}H_{28}OSiNa$, 335.180; found, 335.181.

Example 23

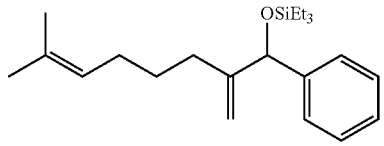

Triethyl-(7-methyl-2-methylene-1-phenyl-oct-6-enyloxy)-silane (2t')

A 10 mL round bottom flask and a stir bar were oven-dried and brought into a glove box. Ni(cod)$_2$ (27.5 mg, 0.2 mmol, 20 mol %) and dicyclohexylphenylphosphine (55 mg, 0.4 mmol, 40 mol %) were added to the round bottom flask, the flask was sealed with a septum, and the sealed flask was brought out of the glove box and connected to an argon line. The catalyst mixture was dissolved in toluene (1.0 mL) under argon and stirred 5 min at room temperature. 7-Methyl-1,7-octadiene (825 μL, 5 mmol, 1000 mol %) was added. Triethylamine (418 μL, 3 mmol, 600 mol %) was added. TESOTf (197 μL, 0.875 mmol, 175 mol %) was added. Benzaldehyde (51 μL, 0.5 mmol, 100 mol %) in 1.5 mL toluene was added to the reaction mixture over 6 min. The mixture was stirred at room temperature for 18 h. The mixture was filtered through a plug of silica gel. Solvent was removed under reduced pressure and $^1$H NMR of the crude mixture indicated the ratio of allylic:homoallylic product was 71:29. Purification via flash chromatography on silica afforded the product in 50% isolated yield as a colorless oil.

The reaction can be run according to general procedure 3, which also afforded the product in similar yield.

$^1$H NMR (400 MHz, CDCl$_3$, δ): 7.40 (d, J=7.0 Hz, 2H); 7.34 (t, J=7.8 Hz, 2H); 7.27 (t, 1H); 5.26 (bs, 1H); 5.18 (bs, 1H); 5.10 (t, J=7.2 Hz, 1H); 4.81 (bs, 1H); 1.76-2.10 (m, 4H); 1.71 (s, 3H); 1.60 (s, 3H); 1.44 (quintet, J=7.7 Hz); 0.97 (t, J=7.9 Hz, 9H); 0.62 (dq, J=1.5, 7.9 Hz, 6H). $^{13}$C NMR (100 MHz, CDCl$_3$,): 152.1, 143.7, 131.6, 128.1, 127.1, 126.6, 124.8, 109.5, 78.2, 30.4, 28.2, 28.1, 25.9, 17.8, 7.0, 5.0. IR (NaCl, thin film): 2955, 2877, 1647, 1456, 1091, 1067, 743. HRMS-ESI (m/z): [M+Na]$^+$ calcd for C$_{22}$H$_{36}$OSi, 367.243; found, 367.243.

Example 24

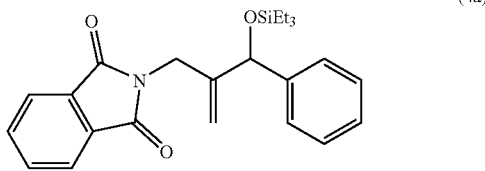

(4a)

The reaction of allylphthalimide (281 mg, 1.5 mmol, 300 mol %) and benzaldehyde (51 μL, 0.5 mmol) with Ni(cod)$_2$, dicyclohexylphenylphosphine (55 mg, 0.4 mmol, 40 mol %) and TESOTf (197 μL, 0.875 mmol), triethylamine in toluene at 35° C. following general procedure 3 above afforded a mixture of allylic and homoallylic products in 67% total yield according to $^1$H NMR of the crude mixture and the ratio of allylic:homoallylic product was 74:26. Purification via flash chromatography on silica afforded the product as a mixture of 4a and the isomerized starting material. $^1$H NMR (400 MHz, CDCl$_3$, δ): 7.77 (dd, J=3.0, 5.4 Hz, 2H); 7.73 (dd, J=3.0, 5.4 Hz, 2H); 7.13-7.41 (m, 5H); 5.36 (s, 1H), 5.30 (s, 1H), 4.99 (s, 1H), 4.26 (d, J=16 Hz, 1H), 4.08 (d, J=16 Hz, 1H), 0.91 (t, J=7.9 Hz, 9H); 0.59 (q, J=7.9 Hz, 6H).

Example 25

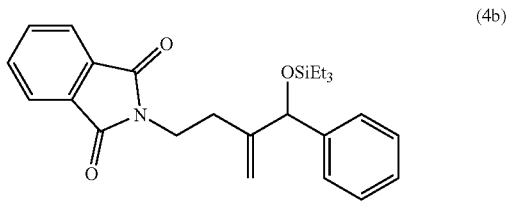

(4b)

The reaction of homoallylphthalimide (1.5 mmol, 300 mol %) and o-anisaldehyde (61 μL, 0.5 mmol) with Ni(cod)$_2$, dicyclohexylphenylphosphine (55 mg, 0.4 mmol, 40 mol %) and TESOTf (197 μL, 0.875 mmol), triethylamine in toluene at 35° C. following general procedure 3 above afforded a mixture of allylic product and homoallylic product in 54% total yield according to $^1$H NMR of the crude mixture and the ratio of allylic:homoallylic product was 71:29. Purification via flash chromatography on silica afforded 4b. $^1$H NMR (400 MHz, CDCl$_3$, δ): 7.81 (dd, J=3.0, 5.4, 2H); 7.70 (dd, J=3.0, 5.4, 2H); 7.26 (d, J=8.7 Hz, 2H); 6.79 (d, J=8.7 Hz, 2H); 5.27 (s, 1H); 5.15 (s, 1H); 4.99 (s, 1H); 3.66-3.86 (m, 2H); 3.78 (s, 3H); 2.33-2.40 (m, 1H); 2.16-2.23 (m, 1H); 0.90 (t, J=7.9 Hz, 9H); 0.57 (q, J=7.9 Hz, 6H). $^{13}$C NMR (100 MHz, CDCl$_3$, δ): 168.4, 158.8, 148.6, 135.2, 134.0, 132.3, 127.7, 123.3, 113.5, 111.8, 77.6, 55.3, 37.2, 29.8, 7.0, 5.0. IR NaCl, thin film): 2954, 2876, 1773, 1715, 1511, 1467, 1431, 1395, 1354, 1247, 1078, 952, 719. HRMS-ESI (m/z): [+Na]$^+$ calcd for C$_{26}$H$_{33}$O$_4$SiNa, 474.2066; found, 474.2071.

Example 26

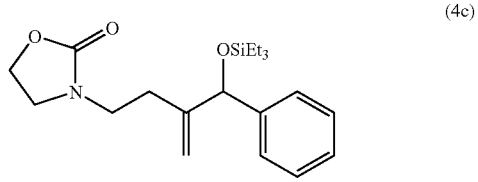

(4c)

The reaction of homoallyloxazolidinone (1.5 mmol, 300 mol %) and benzaldehyde (51 μL, 0.5 mmol) with Ni(cod)$_2$, dicyclohexylphenylphosphine (55 mg, 0.4 mmol, 40 mol %) and TESOTf (197 μL, 0.875 mmol), triethylamine in toluene at room temperature following the general procedure 3 above afforded a mixture of allylic product and homoallylic product in 60% total yield according to $^1$H NMR of the crude mixture and the ratio of allylic:homoallylic product was 83:17. Purification via flash chromatography on silica afforded 4c as a colorless oil. $^1$H NMR (400 MHz, CDCl$_3$, δ): 7.23-7.38 (m, 5H); 5.31 (s, 1H); 5.20 (s, 1H); 5.00 (s, 1H); 4.16-4.21 (m, 2H); 3.19-3.36 (m, 4H); 2.02-2.26 (m, 2H); 0.93 (t, J=7.9 Hz, 9H); 0.60 (q, J=7.8 Hz, 6H). $^{13}$C NMR (100 MHz, CDCl$_3$, δ): 158.4, 148.1, 143.1, 128.2, 127.4, 126.3, 112.0, 78.1, 61.8, 44.3, 42.8, 27.9, 7.0, 4.9. IR (NaCl, thin film): 2955, 2912, 2876, 1753, 1484, 1426, 1265, 1089, 1067, 1044, 1007, 861, 744, 701. HRMS-ESI (m/z): [M+Na]$^+$ calcd for C$_{20}$H$_{31}$NO$_3$N$_a$, 384.1965; found, 384.1951.

Example 27

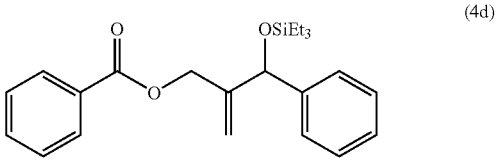

(4d)

The reaction of allylbenzoate (2.5 mmol, 500 mol %) and benzaldehyde (51 μL, 0.5 mmol) with Ni(cod)₂, dicyclohexylphenylphosphine (55 mg, 0.4 mmol, 40 mol %) and TESOTf (197 μL, 0.875 mmol), triethylamine in toluene following general procedure 3 above afforded a mixture of allylic product and homoallylic product in <5% total yield according to ¹H NMR of the crude mixture. The allylic product and homoallylic product were not isolated from the reaction mixture.

Example 28

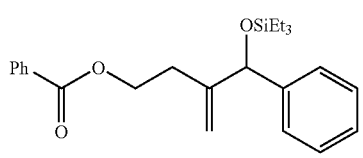

(4e)

The reaction of homoallylbenzoate (1.5 mmol, 300 mol %) and benzaldehyde (51 μL, 0.5 mmol) with Ni(cod)₂, dicyclohexylphenylphosphine (55 mg, 0.4 mmol, 40 mol %) and TESOTf (197 μL, 0.875 mmol), triethylamine in toluene at room temperature following the general procedure 3 above afforded a mixture of allylic product and homoallylic product in 21% total yield according to ¹H NMR of the crude mixture. 4e was subjected to TBAF and the free alcohol was isolated as a colorless oil.

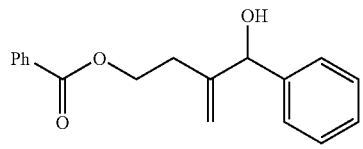

(Desilylated 4e)

¹H NMR (400 MHz, CDCl₃, δ): 8.02 (d, J=7.3 Hz, 2H); 7.58 (t, J=7.3 Hz, 1H); 7.28 (m, 7H); 5.37 (s, 1H); 5.29 (s, 1H); 5.12 (s, 1H); 4.36-4.50 (m, 2H); 2.34-2.51 (m, 2H); 2.29 (br s, 1H). ¹³C NMR (100 MHz, CDCl₃, δ): 166.9, 147.0, 141.8, 133.1, 130.4, 129.7, 128.7, 128.5, 128.0, 126.7, 113.3, 77.6, 63.7, 31.3. IR (NaCl, thin film): 3447, 3063, 3030, 2961, 1717, 1701, 1451, 1316, 1276, 1117, 1071, 1026, 912, 712, 701, 668. HRMS-ESI (m/z): [M+Na]⁺ calcd for C₁₈H₁₈O₃Na, 305.1148; found, 305.1156.

Example 29

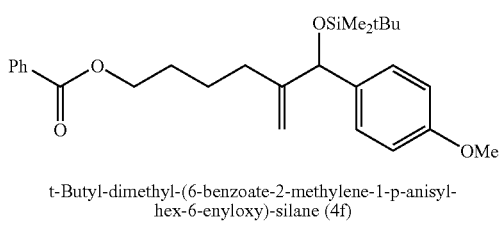

t-Butyl-dimethyl-(6-benzoate-2-methylene-1-p-anisyl-hex-6-enyloxy)-silane (4f)

The reaction of 1-hexen-6-benzoate (510.3 mg, 2.5 mmol, 500 mol %) and o-anisaldehyde (61 μL, 0.5 mmol) with Ni(cod)₂, Cy₂PhP (55 mg, 0.2 mmol, 40 mol %) and TBSOTf (201 μL, 0.875 mmol, 175 mol %), triethylamine in toluene following general procedure 3 above afforded a mixture of allylic product and homoallylic product in 44% total isolated yield after flash chromatography on silica and according to ¹H NMR of the crude mixture the ratio of allylic:homoallylic product was 73:27. The products were isolated together as a mixture.

DEFINITIONS

For convenience, certain terms employed in the specification, examples, and appended claims are listed here.

The term "catalytic amount" is recognized in the art and means a substoichiometric amount relative to a reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The term "aryl" means an aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl). The aryl group may be unsubstituted or substituted by 1 to 3 substituents selected from alkyl, O-alkyl and S-alkyl, OH, SH, —CN, halogen, 1,3-dioxolanyl, $CF_3$, $NO_2$, $NH_2$, $NHCH_3$, $N(CH_3)_2$, NHCO-alkyl, —$(CH_2)_mCO_2H$, —$(CH_2)_mCO_2$-alkyl, —$(CH_2)_mSO_3H$, —NH alkyl, —N(alkyl)₂, —$(CH_2)_mPO_3H_2$, —$(CH_2)_mPO_3(alkyl)_2$, —$(CH_2)_mSO_2NH_2$, and —$(CH_2)_mSO_2NH$-alkyl, wherein alkyl is defined as above and m is 0, 1, 2, or 3. Typical substituted aryl groups include methylphenyl, 4-methoxybiphenyl, 3-chloronaphth-1-yl, and dimethylaminophenyl.

The term "aryl" refers to aromatic groups which have 5-14 ring atoms and at least one ring having a conjugated pi electron system and includes carbocyclic aryl, heterocyclic aryl and biaryl groups, all of which may be optionally substituted. The aryl group may be optionally substituted with 1-6 substituents.

"Carbocyclic aryl groups" are groups which have 6-14 ring atoms wherein the ring atoms on the aromatic ring are carbon atoms. Carbocyclic aryl groups include monocyclic carbocyclic aryl groups and polycyclic or fused compounds such as optionally substituted naphthyl groups.

"Heterocyclic aryl" or "heteroaryl" groups are groups which have 5-14 ring atoms wherein 1 to 4 heteroatoms are ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, indolyl and the like, all optionally substituted.

The term "aralkyl" refers to an alkylene group substituted with an aryl group. Suitable aralkyl groups may include benzyl, picolyl, and the like, and may be optionally substituted.

The aryl portion may have 5-14 ring atoms and the alkyl portion may have up to and including 10 carbon atoms. "Heteroarylalkyl" refers to an alkylene group substituted with a heteroaryl group.

The terms "amine" and "amino" are art-recognized and refer to both unsubstituted and substituted amines, e.g., a moiety that can be represented by the general formula: N(R')(R'')(R''') wherein R', R'', and R''' each independently represent a group permitted by the rules of valence.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The phrase "protecting group" as used herein refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

As used herein, the term "substituted" is contemplated to include all permissible substituents of organic compounds, "permissible" being in the context of the chemical rules of valence known to those of ordinary sldll in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted aldehyde" must still comprise the aldehyde moiety and can not be modified by substitution, in this definition, to become, e.g., a carboxylic acid. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower -carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, lower arylalkyloxyalkyl, and the like.

The term "carbonyl" is recognized in the art and refers to the group, C=O.

The term "carboxyl group" or "carbonyl group" is recognized in the art and can include such moieties as can be represented by the general formula:

wherein X is H, OH, O-alkyl, O-alkenyl, or a pharmaceutically acceptable salt thereof. Where X is O-alkyl, the formula represents an "ester." Where X is OH, the formula represents a "carboxylic acid". In general, where the oxygen atom of the above formula is replaced by sulfur, the formula represents a "thiolcarbonyl" group. Where X is a S-alkyl, the formula represents a "thiolester." Where X is SH, the formula represents a "thiolcarboxylic acid." On the other hand, where X is alkyl, the above formula represents a "ketone" group. Where X is hydrogen, the above formula represents an "aldehyde" group.

The term "acyl" refers to —C(O)R where R is alkyl, heterocycloalkyl, or aryl. The term "lower acyl" refers to where R is lower alkyl. The term $C_1$-$C_4$ acyl refers to where R is $C_1$-$C_4$.

The term "carboxy esters" refers to —C(O)OR where R is alkyl, aryl, aralkyl, cyclic alkyl, or heterocycloalkyl, all optionally substituted.

The term "carboxyl" refers to —C(O)OH.

The terms "alkenyl" and "alkynyl" refer to unsaturated aliphatic groups analogous in length and possible substitution to the alkyls described above, but which contain at least one double or triple carbon-carbon bond, respectively. The term "alkenylalkyl" refers to an alkyl groups substituted with an alkenyl group. The term "alkynylalkyl" refers to an alkyl groups substituted with an alkynyl group.

The term "alkenyl" refers to unsaturated groups which have 2 to 12 atoms and Contain at least one carbon-carbon double bond and includes straight-chain, branched-chain and cyclic groups. Alkenyl groups may be optionally substituted. Suitable alkenyl groups include allyl. "1-Alkenyl" refers to alkenyl groups where the double bond is between the first and second carbon atom.

The term "alkynyl" refers to unsaturated groups which have 2 to 12 atoms and contain at least one carbon-carbon triple bond and includes straight-chain, branched-chain and cyclic groups. Alkynyl groups may be optionally substituted. Suitable alkynyl groups include ethynyl. "1-Alkynyl" refers to alkynyl groups where the triple bond is between the first and second carbon atom.

The term "alkylene" refers to a divalent straight chain, branched chain or cyclic saturated aliphatic group. In one aspect the alkylene group contains up to and including 10 atoms. In another aspect the alkylene chain contains up to and including 6 atoms. In a further aspect the alkylene groups contains up to and including 4 atoms. The alkylene group can be either straight, branched or cyclic. The alkylene may be optionally substituted with 1-3 substituents.

The term "alkoxy-" or "alkyloxy-" refers to the group alkyl-O—.

The term "electron-withdrawing group" is recognized in the art and as used herein means a functionality which draws electrons to itself more than a hydrogen atom would at the same position. Exemplary electron-withdrawing groups include carbonyl groups (e.g., ketone, esters, aldehydes), sulfonyl, trifluoromethyl, nitro, cyano, and the like.

What is claimed:

1. A method, comprising:
reacting an alkene and an aldehyde to form an allylic alcohol or precursor of an allylic alcohol, provided that the aldehyde is not formaldehyde,
wherein the alkene has the structure

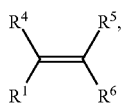

and any of $R^1$, $R^4$, $R^5$, and $R^6$ can be the same or different from any other, and each can be independently hydrogen, optionally substituted alkyl, optionally substituted cycloalkyl, optionally substituted aralkyl, optionally substituted heteroaralkyl, optionally substituted alkenylalkyl, or optionally substituted alkynylalkyl; and
wherein the aldehyde has the structure

and $R^2$ can be optionally substituted alkyl, optionally substituted cycloalkyl, optionally substituted aryl, optionally substituted heteroaryl, optionally substituted aralkyl, optionally substituted heteroaralkyl, optionally substituted alkenylalkyl, or optionally substituted alkynylalkyl.

2. A method, comprising:
reacting an alkene and an aldehyde to form an allylic alcohol or precursor of an allylic alcohol, provided that the alkene is not an electron deficient alkene,
wherein the alkene has the structure

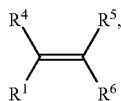

and any of $R^1$, $R^4$, $R^5$, and $R^6$ can be the same or different from any other, and each can be independently hydrogen, optionally substituted alkyl, optionally substituted cycloalkyl, optionally substituted aralkyl, optionally substituted heteroaralkyl, optionally substituted alkenylalkyl, or optionally substituted alkynylalkyl; and
wherein the aldehyde has the structure

and $R^2$ can be optionally substituted alkyl, optionally substituted cycloalkyl, optionally substituted aryl, optionally substituted heteroaryl, optionally substituted aralkyl, optionally substituted heteroaralkyl, optionally substituted alkenylalkyl, or optionally substituted alkynylalkyl.

3. A method, comprising:
reacting an alkene and an aldehyde in the presence of a catalyst to form an allylic alcohol or precursor of an allylic alcohol,
wherein the catalyst is a compound comprising a Group 9, Group 10, or Group 11 metal;
wherein the alkene has the structure

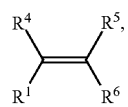

and any of $R^1$, $R^4$, $R^5$, and $R^6$ can be the same or different from any other, and each can be independently hydrogen, optionally substituted alkyl, optionally substituted cycloalkyl, optionally substituted aralkyl, optionally substituted heteroaralkyl, optionally substituted alkenylalkyl, or optionally substituted alkynylalkyl; and
wherein the aldehyde has the structure

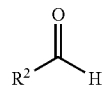

and $R^2$ can be optionally substituted alkyl, optionally substituted cycloalkyl, optionally substituted aryl, optionally substituted heteroaryl, optionally substituted aralkyl, optionally substituted heteroaralkyl, optionally substituted alkenylalkyl, or optionally substituted alkynylalkyl.

4. The method of claim 1, wherein the alkene is an alpha-olefin.

5. The method of claim 1, wherein the alkene is not positioned adjacent to an electron-deficient functionality.

6. The method of claim 1, further comprising a catalyst.

7. The method of claim 6, wherein the catalyst comprises a Group 9, Group 10, or Group 11 metal.

8. The method of claim 2, wherein the alkene is an alpha-olefin.

9. The method of claim 2, further comprising a catalyst.

10. The method of claim 9, wherein the catalyst comprises a Group 9, Group 10, or Group 11 metal.

11. The method of claim 3, wherein the alkene is an alpha-olefin.

12. The method of claim 3, wherein the alkene is not positioned adjacent to an electron-deficient functionality.

13. The method of claim 3, wherein the catalyst comprises cobalt, rhodium, iridium, nickel, palladium, platinum, copper, silver, or gold.

14. The method of claim 3, further comprising a phosphine.

* * * * *